(12) United States Patent
Borden et al.

(10) Patent No.: US 6,971,791 B2
(45) Date of Patent: Dec. 6, 2005

(54) IDENTIFYING DEFECTS IN A CONDUCTIVE STRUCTURE OF A WAFER, BASED ON HEAT TRANSFER THERETHROUGH

(75) Inventors: Peter G. Borden, San Mateo, CA (US); Ji-Ping Li, Fremont, CA (US)

(73) Assignee: Boxer Cross, INC, Santa Clara, CA (US)

( * ) Notice: Subject to any disclaimer, the term of this patent is extended or adjusted under 35 U.S.C. 154(b) by 148 days.

(21) Appl. No.: 10/090,287

(22) Filed: Mar. 1, 2002

(65) Prior Publication Data

US 2003/0165178 A1 Sep. 4, 2003

(51) Int. Cl.$^7$ .......................... G01R 31/26; G01N 21/00
(52) U.S. Cl. ..................... 374/5; 374/45; 374/57; 324/765; 324/751; 324/752
(58) Field of Search ................. 374/4–7, 45, 57, 374/43, 44, 120; 324/752, 765, 751, 501

(56) References Cited

U.S. PATENT DOCUMENTS

| | | | |
|---|---|---|---|
| 3,462,602 A | 8/1969 | Apple ..................... 250/83 |
| 3,803,413 A | * 4/1974 | Vanzetti et al. | |
| 3,909,602 A | 9/1975 | Micka ..................... 235/151 |
| 3,930,730 A | 1/1976 | Laurens et al. ............ 356/106 |
| 4,201,087 A | * 5/1980 | Akita et al. | |
| 4,243,327 A | 1/1981 | Frosch et al. ............. 356/432 |
| 4,255,971 A | * 3/1981 | Rosencwaig | |
| 4,455,741 A | 6/1984 | Kolodner ................... 29/574 |
| 4,466,748 A | 8/1984 | Needham .................. 374/129 |
| 4,468,136 A | 8/1984 | Murphy et al. ............. 374/45 |
| 4,521,118 A | 6/1985 | Rosencwaig ................ 374/5 |
| 4,552,510 A | 11/1985 | Rosencwaig ................ 374/7 |
| 4,579,463 A | 4/1986 | Rosencwaig et al. ......... 374/57 |
| 4,632,561 A | 12/1986 | Rosencwaig et al. ....... 356/432 |
| 4,634,290 A | 1/1987 | Rosencwaig ................ 374/5 |
| 4,636,088 A | 1/1987 | Rosencwaig et al. .......... 374/5 |
| 4,710,030 A | 12/1987 | Tauc et al. ................ 356/445 |
| 4,795,260 A | 1/1989 | Schuur et al. ............. 356/400 |
| 4,950,990 A | 8/1990 | Moulder ................... 324/224 |
| 4,975,141 A | 12/1990 | Greco et al. .............. 156/626 |

(Continued)

FOREIGN PATENT DOCUMENTS

| | | | |
|---|---|---|---|
| EP | 0 718 595 | 12/1995 | |
| JP | 05006929 A | 1/1993 | ......... H01L/21/66 |
| JP | 2000009443 A | 1/2000 | |
| WO | 97/08536 | 6/1997 | ......... G01N/21/00 |
| WO | 99/64880 | 12/1999 | ......... G01R/31/26 |

OTHER PUBLICATIONS

Jackson, "Classical Electrodynamics", John Wiley & Sons, Inc., (month unavailable), 1967, pp. 222–226.

Rosenewaig et al. "Detection of Thermal Waves Through Optical Reflectance", Appl Phys. Lett. 46, Jun. 1985, pp. 1013–1015.

(Continued)

*Primary Examiner*—Gail Verbitsky
(74) *Attorney, Agent, or Firm*—Silicon Valley Patent Group LLP

(57) ABSTRACT

Heat is applied to a conductive structure that includes one or more vias, and the temperature at or near the point of heat application is measured. The measured temperature indicates the integrity or the defectiveness of various features (e.g. vias and/or traces) in the conductive structure, near the point of heat application. Specifically, a higher temperature measurement (as compared to a measurement in a reference structure) indicates a reduced heat transfer from the point of heat application, and therefore indicates a defect. The reference structure can be in the same die as the conductive structure (e.g. to provide a baseline) or outside the die but in the same wafer (e.g. in a test structure) or outside the wafer (e.g. in a reference wafer), depending on the embodiment.

38 Claims, 19 Drawing Sheets

U.S. PATENT DOCUMENTS

| | | | |
|---|---|---|---|
| 4,996,659 A | | 2/1991 | Yamaguchi et al. ........ 714/736 |
| 5,042,951 A | | 8/1991 | Gold et al. .................. 356/369 |
| 5,074,669 A | | 12/1991 | Opsal .......................... 356/447 |
| 5,128,864 A | * | 7/1992 | Waggener et al. |
| 5,149,978 A | | 9/1992 | Opsal et al. ................. 250/234 |
| 5,159,412 A | | 10/1992 | Willenborg et al. ........ 356/445 |
| 5,181,080 A | | 1/1993 | Fanton et al. ............... 356/381 |
| 5,228,776 A | * | 7/1993 | Smith et al. |
| 5,304,931 A | * | 4/1994 | Flamig et al. |
| 5,377,006 A | | 12/1994 | Nakata ........................ 356/349 |
| 5,408,327 A | | 4/1995 | Geiler et al. ................ 356/532 |
| 5,430,548 A | | 7/1995 | Hirio et al. .................. 356/394 |
| 5,454,004 A | | 9/1995 | Leger ........................... 372/99 |
| 5,574,562 A | | 11/1996 | Fishman et al. ............. 356/432 |
| 5,652,716 A | | 7/1997 | Battersby ...................... 703/13 |
| 5,657,754 A | | 8/1997 | Rosencwaig ................ 128/633 |
| 5,667,300 A | | 9/1997 | Mandelis et al. ............. 374/43 |
| 5,741,614 A | | 4/1998 | McCoy et al. ................ 430/30 |
| 5,761,082 A | | 6/1998 | Miura-Mattausch ......... 703/14 |
| 5,764,363 A | | 6/1998 | Ooki et al. .................. 356/364 |
| 5,790,251 A | | 8/1998 | Hagiwara .................... 356/351 |
| 5,877,860 A | | 3/1999 | Borden ........................ 356/376 |
| 5,883,518 A | | 3/1999 | Borden ........................ 324/752 |
| 5,966,019 A | | 10/1999 | Borden ........................ 324/752 |
| 5,978,074 A | | 11/1999 | Opsal et al. ................... 356/72 |
| 6,049,220 A | * | 4/2000 | Borden et al. .............. 324/765 |
| 6,054,868 A | | 4/2000 | Borden et al. .............. 324/752 |
| 6,081,334 A | | 6/2000 | Grimbergen et al. ........ 356/357 |
| 6,154,280 A | | 11/2000 | Borden ........................ 356/376 |
| 6,169,601 B1 | | 1/2001 | Eremin et al. .............. 356/240 |
| 6,178,020 B1 | * | 1/2001 | Schultz et al. |
| 6,281,027 B1 | | 9/2001 | Wei et al. ...................... 438/14 |
| 6,323,951 B1 | | 11/2001 | Borden et al. .............. 356/502 |
| 6,327,035 B1 | | 12/2001 | Li et al. ...................... 356/432 |
| 6,330,361 B1 | * | 12/2001 | Mitchell et al. |
| 6,336,969 B1 | | 1/2002 | Yamaguchi et al. ........... 117/7 |
| 6,395,563 B1 | | 5/2002 | Eriguchi ......................... 438/7 |
| 6,426,644 B1 | | 7/2002 | Borden et al. .............. 324/765 |
| 6,483,594 B2 | | 11/2002 | Borden et al. .............. 356/502 |
| 6,486,965 B1 | | 11/2002 | Kim ............................ 356/626 |
| 6,489,624 B1 | | 12/2002 | Ushio et al. ................. 250/559 |
| 6,489,801 B1 | | 12/2002 | Borden et al. .............. 324/766 |
| 6,528,333 B1 | | 3/2003 | Jun et al. ....................... 438/16 |
| 6,559,942 B2 | | 5/2003 | Sui et al. ..................... 356/369 |
| 6,694,284 B1 | | 2/2004 | Nikoonahad et al. ....... 702/155 |
| 6,734,968 B1 | | 5/2004 | Wang et al. ................. 356/369 |
| 2002/0126732 A1 | * | 9/2002 | Shakouri et al. |
| 2002/0186045 A1 | * | 12/2002 | Cox |
| 2003/0036231 A1 | * | 2/2003 | Bhattacharya et al. |
| 2003/0096436 A1 | * | 5/2003 | Satya et al. ................... 438/11 |
| 2003/0155927 A1 | * | 8/2003 | Pinto et al. .................. 324/501 |

OTHER PUBLICATIONS

Rosenewaig, "Thermal–Wave Imaging", SCIENCE, vol. 218, No. 4569, Oct. 1982, pp. 223–228.

Opsal et al. "Thermal–Wave Detection and Thin–Film Thickness Measurements with Laser Beam Deflection", Applied Optics, vol. 22, No. 20, Oct. 1983, pp. 3169–3176.

Rosenewaig, "Thermal Wave Characterization and Inspection of Semiconductor Materials and Devices", Chapter 5 (pp. 97–135) of Photoacoustic and Thermal Wave Phenomena in Semiconductors, North Holland (month unavailable) 1987.

"Process Monitoring System," Quantox Product Brochure, 3 pg, prior to Jun. 10, 1998.

J. Opsal, "High Resolution Thermal Wave Measurements and Imaging of Defects and Damage in Electronic Materials" Photoacoustic and Photothermal Phenomena II, Springer Series in Optical Sciences, vol. 62, Springer Verlag Berlin, Heidelberg, 1990.

J. Kolzer et al "Thermal Imaging and Measurement Techniques for Electronic Materials and Devices" Microelectronic Engineering, vol. 31, 1996 (month unknown) pp. 251–270.

C. Martinsons et al. "Recent progress in the measurement of thermal properties of hard coatings" thin Solid Films, vol. 317, Apr. 1998, 455–457.

S. Wolf and R. N. Tauber, "Silicon Processing For The VLSI Era", vol. 1, 1986, pp. 388–399.

Yaozhi Hu and Sing Pin Tay, "Spectroscopic ellipsometry investigation of nickel silicide formation by rapid thermal process", J. Vac. Sci. Technology, American Vacuum Soc. May/Jun. 1998, pp. 1820–1824.

Quality Today News, article entitled "In–Line Metrology SEM System with 3D Imaging" dated Jan. 10, 2000 and published at http://www.qualitytoday.com/Jan.–00–news/011000–3.htm before Apr. 4, 2001.

Bristow, Thomas C. and Dag Lindquist, "Surface Measurements With A Non–Contact Nomarski–Profiling Instrument", Interferometric Metrology, SPIE vol. 816, Aug. 1987, p. 106–110.

Walter G. Driscoll and William Vaughan, "Handbook of Optics", 1978, pp. 8–42, 8–43, 8–107, and 10–72 to 10–77.

Charles Kittel, "Introduction to Solid State Physics", Fourth Edition, John Wiley & Sons, published prior to Mar. 1, 2002, pp. 262–264.

Rolf E. Hummel, "Electronic Properties of Materials, An Introduction For Engineers", published prior to Mar. 1, 2002, pp. 137–145.

H.S. Carslaw and J.C. Jaegar, "Conduction of Heat in Solids", Second Edition, published prior to Mar. 1, 2002, pp. 64–66.

"Process Monitoring System", Quantox Product Brochure, 3 pages, published prior to Mar. 1, 2002.

A. Rosenewaig, "Thermal Wave Measurement of Thin–Film Thickness", 1986 American Chemical Society, pp. 182–191.

"Thin–Film Thickness Mesurements with Thermal Waves", Journal De Physique, Oct. 1983, pp. C6–483 –C6–489.

W. L. Smith et al. "Thermal–wave Measurements and Monitoring of TaSix Silicide Film Properties" J. Vac. Technol.B2(4), Oct.–Dec. 1984, pp. 710–713.

A. Salnick et al., Nonlinear Fundamental Photothermal Response in 3D Geometry: Experimental Results for Tungsten (believed to be prior to Mar. 1, 2002).

S. Ameri et al., "Photo–Displacement Imaging", Mar. 30, 1981, pp. 337–338.

L. Chen et al., "Thermal Wave Studies of Thin Metal Films Using the Meta–Probe–A New Generation Photothermal System" 25th Review of Progress in QNDE, Snowbird, UT 19–24 Jul. 1998, pp. 1–12.

P. Alpem and S. Wurm, "Modulated Optical Reflectance Measurements on Bulk Metals and Thin Metallic Layers", J. Appl. Phys. 66(4), Aug. 15, 1989, pp. 1676–1679.

J. Opsal, "The Application of Thermal Wave Technology to Thickness and Grain Size Monitoring of Aluminum Films", SPIE vol. 1596 Metalization Performance and Reliability Issues for VLSI and ULSI (1991), pp. 120–131.

A. Rosenwaig, "Process Control in IC Manufacturing With Thermal Waves", Review of Progress in Quantitative Nondestructive Evaluation, vol. 9, 1990, pp. 2031–2037.

K. Farnaam, "Measurement of Aluminum Alloy Grain Size on Product Wafers and its Correlation to Device Reliability", 1990 WLR Final Report, pp. 97–106.

B.C. Forget et al., "High Resolution AC Temperature Field Imaging", Electronic Letters 25th Sep. 1997, vol. 33 No. 20, pp. 1688–1689.

C. Paddock et al., "Transient Thermoreflectance from Metal Films", May 1986 vol. 11, No. 5 Optical Letters, pp. 273–275.

C. Paddock et al., "Transient Thermoreflectance from Metal Films", J. Appl. Phys. 60(1), Jul. 1, 1986, pp. 285–290.

Per–Eric Nordail et al. "Photothermal Radiometry", Physic Scripts, vol. 20, 659–662, 1979.

A. Rosenwaig, "Thermal Wave Monitoring and Imaging of Electronic Materials and Devices", pp. 73–109, (believed to be prior to Mar. 1, 2002).

A. Rosenwaig, "Applications of Thermal–Wave Physics to Microelectronics", VLSI Electronics, Mircostructure Science vol. 9, pp. 227–288 1985.

W. Lee Smith et al., "Voids, Notches and Micros–cracks in Al Metallization Detected by Nondestructive Thermal Wave Imaging", Jun. 23m 1989, pp. 211–221.

W. Lee Smith et al., Imaging of Subsurfaces Defects in ULSI Metalization (Al Voids Sl Precipitates, Silicide Instability) and Sl Substrates (D Defects), Technical Proceedings Simicon/Japan 1992, Nippon Convention Center, Japan pp. 238–246.

W. Lee Smith, "Nondestructive Thermal Wave Imaging of Voids & Microcracks in Aluminum Metallization", 1989 WLR Final Report, pp. 55–68.

W. Lee Smith, "Direct Measurement of Stress–Induced Void Growth by Thermal Wave Modulated Optical Reflectance Imaging", 1991 IEEE/IRPS, pp. 200–208.

W. Lee Smith, "Evaluating Voids and Microcracks in Al Metalization", Semiconductor International, Jan. 1990, pp. 232–237.

C. G. Welles et al., "High–Resolution Thermal Wave Imaging of Surface and Subsurface Defects in IC Metal Lines", Materials Research Society, SF Marriott, Apr. 27–May 1, 1992, pp. 1187–1191.

L. Fabbri et al., "Analysis of Local Heat Transfer Properties of Tape–cast AlN Ceramics Using Photothermal Reflectance Microscopy", 1996 Chapman & Hall, pp. 5429–5436.

J.A. Batisla et al., "Biased MOS–FET and Polycrystalline Silicon Tracks Investigated by Photothermal Reflectance Microscopy", pp. 468–469.

L. Chen et al., "Meta–Probe: A New Generation Photothermal System For Thin Metal Films Characterization" (believed to be prior to Mar. 1, 2002).

L. Chen et al., "Thermal Wave Studies of Thin Metal Films and Structures".

9th International Conference on Photoacoustic and Photothermal Phenomena Conference Digest, Jun. 27–30, 1996 Nanjing, P.R. China, pp. 81.

R. S. Sharpe, Research Techniques in Nondestructive Testing vol. VII, Academic Press 1984, pp. 158–365.

R. L. Thomas et al., "Thermal Wave Imaging For Nondestructive Evaluation" 1982 Ultrasonic Symposium, pp. 586–590.

G. Slade Cargill III, "Electron–Acoustic Microscopy", Physics Today, Oct. 1981, pp 27–32.

A. Rosenewaig, "Thermal Wave Microscopy", Solid State Technology, Mar. 1982, pp 91–97.

Eric A. Ash, "Acoustical Imaging" vol. 12, Plenium Press, Jul. 19–22, 1982, pp 61–65.

* cited by examiner

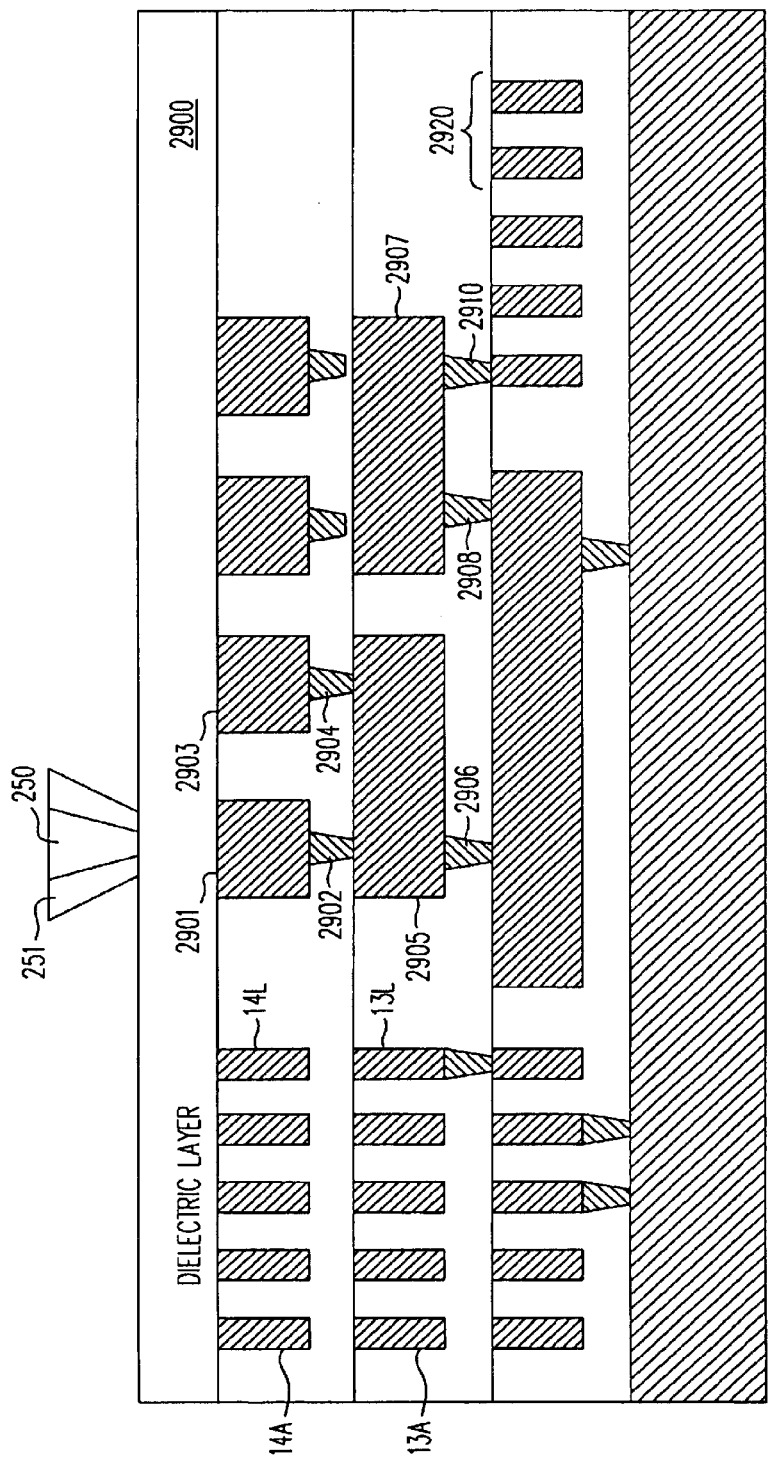
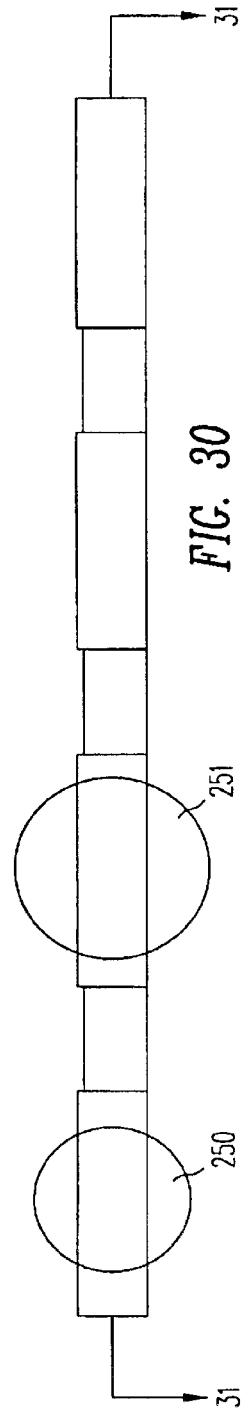
FIG. 29
FIG. 30

IDENTIFYING DEFECTS IN A CONDUCTIVE STRUCTURE OF A WAFER, BASED ON HEAT TRANSFER THERETHROUGH

CROSS-REFERENCE TO RELATED APPLICATIONS

This application is related to and incorporates by reference herein in their entirety the following commonly owned U.S. patent applications:

Ser. No. 09/095,805 entitled "AN APPARATUS AND METHOD FOR MEASURING A PROPERTY OF A LAYER IN A MULTI-LAYERED STRUCTURE", filed Jun. 10, 1998, by Peter G. Borden et al., which is now issued as U.S. Pat. No. 6,054,868;

Ser. No. 09/521,232 entitled "EVALUATING A PROPERTY OF A MULTI-LAYERED STRUCTURE", filed Mar. 8, 2000, by Peter G. Borden et al.;

Ser. No. 09/544,280 entitled "AN APPARATUS AND METHOD FOR EVALUATING A WAFER OF SEMICONDUCTOR MATERIALS", filed Apr. 6, 2000, by Peter G. Borden et al., which is a continuation of Ser. No. 09/095,804, filed Jun. 10, 1998, and now issued as U.S. Pat. No. 6,049,220; and Ser. No. 10/090,062, entitled "EVALUATING A MULTI-LAYERED STRUCTURE FOR VOIDS", filed concurrently herewith, by Peter G. Borden et al.

Ser. No. 10/090,316, entitled "AN APPARATUS AND METHOD FOR MEASURING A PROPERTY OF A LAYER IN A MULTILAYERED STRUCTURE", filed concurrently herewith, by Peter G. Borden et al.

BACKGROUND

Integrated circuits (ICs) use metal lines to connect the various circuit elements together. Because a small size of the circuit elements and a high density of connections are required, it is necessary to use several levels of metal lines. Each level contains a planar structure of metal lines, with layers of an insulator such as silicon dioxide used to separate the levels from one another.

It is necessary to interconnect the layers to one another, to enable current to flow between the layers. These interconnections are called vias. Vias are located in small holes formed in the insulator, and may be 0.13 $\mu$m in diameter or larger. These holes are filled with a metal to form an interconnection between metal lines in different layers. Such interconnections must be continuous from a lower level of metal to a higher level. If an interconnection is not continuous, the via will be "open". This defect may cause failure of the integrated circuit.

Open vias can result from a number of process problems. For example, the process of filling the small holes with metal may not fully fill a hole. A residue from a previous process step may impede connection, or the residue may be corrosive and etch away a connection that was properly formed. Such a problem might result in an open via. Also, the formation of subsequent layers of metal requires thermal process steps that may cause a properly formed via connection to "pull back", leaving a partial connection.

In addition, the formation of a patent layer of metal on top of another layer requires registration of the lithographic pattern. If the pattern is misaligned, vias from one layer may not land or only partially land onto an underlying metal line, resulting in an "unlanded" or "partially landed" via, which forms an open electrical connection, or only a partial electrical connection.

A number of methods of testing vias are available. One method of reliably testing interconnections is electrical testing. For example, a via chain is fabricated and probed for continuity. A via chain is a set of short line segments of conductive material alternating between two layers, connected with vias.

FIG. 1 shows such a via chain 100 as a multi-level interconnect structure formed in a wafer with two layers 113 and 114 formed over a substrate 110. The wafer may have transistors and other devices fabricated within it. Various interconnect lines 131a–131f and 132a–132n may be made of a metal such as copper, and are embedded within interlayer dielectric layers 111 and 112. Vias 133a–133l are shown that interconnect the various segments in layers 113 and 114 to one another. Metal line segments 131a–131f in layer 114 may be 5 $\mu$m long and 0.25 $\mu$m wide. Metal line segments 132a–132n in layer 113 are also of the same dimensions in this example. These segments are connected to form a chain, by vias 133a–133l.

The conductivity of such a chain can be measured by use of probes 140a and 140b that contact chain 100 at the ends of the via chain. To measure the continuity of the chain, an electric current is passed therethrough and measured. This method allows a single measurement to determine the continuity of a large number of vias in the chain. However, such probing has a number of drawbacks when used during manufacturing. First, the just-described "contact" method requires a large area in a production wafer to hold a via chain that is otherwise not a part of a circuit being manufactured. Second, the contact method requires probes to make a contact with structure 200 (FIGS. 3 and 4), which may be undesirable during fabrication, since any contact can generate particles and contamination. Third, the contact method cannot be used if a dielectric layer covers the metal lines in layer 113 because the probes need to be in electrical contact with the two ends of the structure 100. Finally, the contact method cannot isolate individual vias or evaluate a small number of vias in the via chain (unless more complex matrix structures are built).

Other methods of examining vias in a wafer relate to various applications of scanning electron microscopes (SEMs). One of these methods is called voltage contrast. Suppose, for example, that vias 133b and 133c are both open. Metal line 132b will then be electrically floating. Under SEM scanning, this segment 132b will charge with electrons and therefore stand out in an SEM image. The limitation of a voltage contrast is that it cannot be used with partially failed vias, since any via continuity in a partially failed via will discharge the charge from the segment. Also, this method cannot be used once a dielectric layer (not shown in FIG. 1) is formed over the segment, since the dielectric will charge up. Therefore, voltage contrast is only usable when the top layer is a metal layer, and cannot evaluate via problems induced by the process of formation of subsequent layers.

Another SEM method is sectioning. A sample wafer is broken, or a focused ion beam is used to cut away material, exposing a side view of the via. The SEM can then image the via. This method has limitations of being destructive and slow, and is therefore limited to post-analysis of failures.

Another method was disclosed by Smith et al. in U.S. Pat. No. 5,228,776 that is incorporated herein by reference as background. In this patent, a modulated laser beam creates a thermal wave in a metal line. Specifically, Smith et al. state "By this arrangement, the pump beam can be focused on a metal line in one layer while the probe beam is focused on a line in a different layer. Using this approach, it can be relatively easy to find a flaw in a via which is used to connect the two lines." Smith et al. also state that ". . . the assignee's Thermaprobe Imager device is a non-contact technique. However, identification of defective vias has been hampered because the surfaces associated with defective vias are often not optically flat. More particularly, the surfaces can be dimpled, angles, rough or otherwise geometrically distorted and therefore tend to scatter light making reflected power measurements difficult." Smith et al. further state "First, both the pump and probe beams can be focused on optically flat surfaces even if there are intermediate geometrically distorted surfaces associated with a defect."

Smith et al.'s method suffers from two drawbacks. First, thermal waves can reflect from interfaces, such as the end of a line, a bend in a line, or a via connection. Such reflections can perturb measurements based on thermal waves that are described by Smith et al. Second, Smith et al. require that the two laser beams must be independently focused at different sites, which can require complicated optical positioning that varies with circuit geometry.

SUMMARY

In accordance with the invention, heat is applied to a conductive structure that includes one or more vias, and the temperature of the conductive structure is measured. The measurement is made either at the point of heat application, or close enough to the point of heat application such that the temperature at the point of measurement is affected by the applied heat. Good vias that are well connected to conductive regions (such as line segments in a via chain) act as thermal shunts, increasing the flow of heat from the point of application. Defective vias and/or defective line segments that are poorly connected to (or even disconnected from) the point of heat application fail to conduct heat, and therefore get heated up. For this reason, the measured temperature indicates the integrity (or defectiveness) of vias and line segments in the conductive structure.

A higher temperature measurement indicates a reduced heat transfer from the point of application and, hence, a defect in the conductive structure e.g. a poor quality via or a poor quality line segment. Once a defect is found, a poor quality line segment can be distinguished from a poor quality via by any method, e.g. by manual inspection through a microscope. Depending on the fabrication process, such manual inspection may be skipped, e.g. if it is known from experience that a poor quality via is more likely than a poor quality line segment.

One or more beams of electromagnetic radiation may be used to apply heat and/or to measure temperature, depending on the embodiment. For example, a laser beam may be used to inject heat into the conductive structure which could be, e.g. a chain of vias. Such a laser beam (also called "heating beam") may have a fixed intensity, or alternatively may have its intensity modulated, e.g. at a predetermined frequency. Another laser beam (also called "probe beam") may be used to measure reflectance of the via chain, thereby to determine the temperature thereof.

Depending on the embodiment, instead of a probe beam, a thermal imager with a microscope may be used for temperature measurement. Also, instead of using a heating beam, heat may be applied by an electron beam or other heat source, eliminating the need for a laser in certain embodiments. However, an electron beam has the drawback of requiring the conductive structure at the point of heat application to be exposed, while a laser beam can be used in the presence of a transparent dielectric covering the conductive structure.

In one embodiment, a single temperature measurement on a wafer being evaluated is used to identify the presence of a defect in a via chain e.g. by comparison with a predetermined limit (which may be set by experiments on reference wafers).

In another embodiment, scanning such a measurement along a line parallel to the via chain provides a signal that varies as a function of the spatial location of vias in the via chain. For example if vias are located at regular intervals along the chain, a periodic function is obtained when scanning the measurement. The measured signal's periodicity in intensity (over the length of a conductive structure) is analyzed (either manually or automatically), to determine the quality of via chains as a whole in this embodiment.

A non-destructive method of one embodiment uses two laser beams as described above. Such methods may be used on any conductive structure, even when the width of the conductive structure is smaller than the smallest beam's diameter. Moreover, such methods may be used on lines and vias buried under one or more transparent dielectric layers, and still effectively identify defective vias.

Several of the embodiments described herein do not have the drawback of reflections from trace boundaries that occur in the prior art which is based on generation of thermal waves, because no waves are generated in these embodiments. Heating and measurement of the type described herein may be done at the same site, e.g. by using two coaxial laser beams in some embodiments. Therefore, two beams of the type described herein need not each be independently positioned relative to the geometry of the conductive structure, as may be required in some prior art. Depending on the embodiment, two beams (which may or may not be laser beams) can be positioned with a predetermined distance of separation there-between, instead of the two beams being coincident. The distance of separation may be small enough for spots formed by the two beams on a wafer to overlap, or the distance may be large enough for the spots to be completely separated from one another, depending on the implementation.

BRIEF DESCRIPTION OF THE DRAWINGS

FIG. 29 illustrates, in a cross-sectional view, evaluation of a conductive structure that is covered by a dielectric layer, using the method of FIG. 2.

FIG. 30 illustrates, in a plan view, another embodiment in which a heating laser beam is separated from a measurement laser beam by a predetermined distance, during a scan across a via chain.

DETAILED DESCRIPTION

Figure 1:
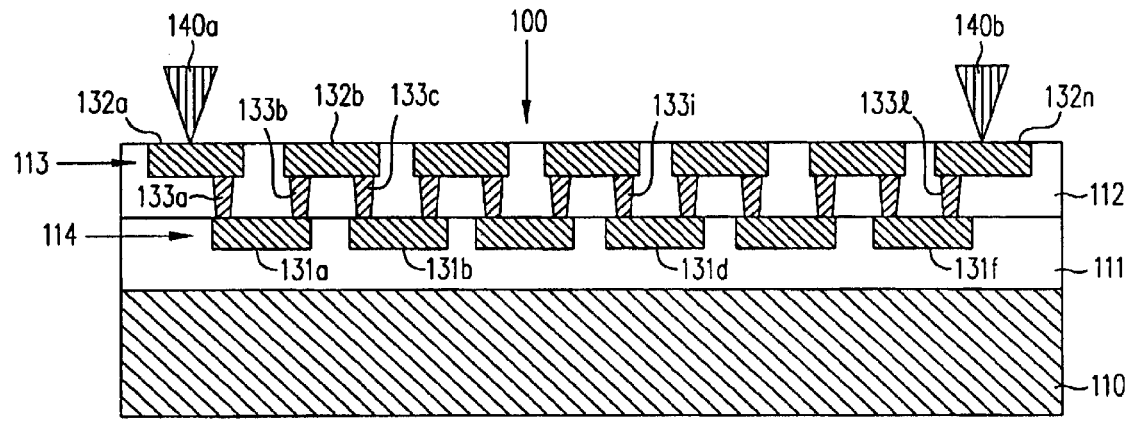
FIG. 1 illustrates, in a cross-sectional view, a multiple level interconnect structure in a semiconductor wafer being evaluated by electrical probes in contact with the structure, in a method of prior art.
Figure 2:
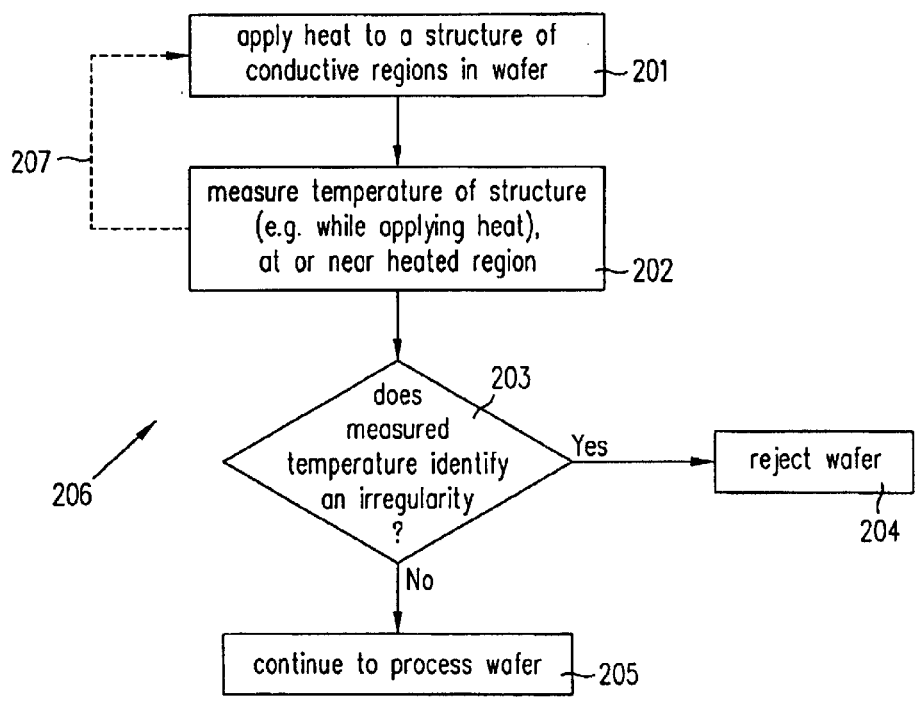
FIG. 2 illustrates, in a flowchart, acts performed by a method in one embodiment of the invention to identify defects in a structure that includes one or more vias.

In accordance with the invention, heat is applied to a structure of conductive regions in a wafer, that are interconnected by one or more vias (see act 201 in FIG. 2). Thereafter, the temperature at or near the point of heat application is measured (see act 202), either during application of heat, or immediately thereafter depending on the embodiment. Thereafter in act 203, the measured temperature is checked to identify an irregularity (e.g. by comparison with a predetermined limit, or by finding aperiodicity in a scan of a periodic structure). If an irregularity is found in the structure, the wafer is rejected as illustrated by act 204. If there is no irregularity, the wafer is further processed in the wafer fabrication process, as illustrated by act 205.

The measured temperature identifies the irregularities because the vias act as thermal shunts, increasing the flow of heat from the point of application, thereby lowering the measured temperature as compared to the temperature measured in the presence of defects in the vias. Specifically, when a defect is present, the defective vias are not able to dissipate as much heat as normal (non-defective) vias. Therefore, the presence of a defective via is indicated by a higher temperature.

Note, however, an increased temperature measurement may indicate other defects in such a conductive structure, such as a narrowed trace. If all of the traces (also called "line segments") are within their manufacturing tolerances, a defective via is indicated by a temperature that is higher than the temperature measured in a non-defective structure, such as a reference wafer. Two typical ways of identifying a poor quality trace are (1) electrical probing of the conductive structure by using contact probes, and (2) the FIB-SEM method wherein an ion beam is used to cut a hole and then the section is imaged with a scanning electron microscope (SEM). Furthermore, a poor quality trace can in many cases be distinguished, by manual inspection through a microscope.

When a defect in a conductive structure is indicated by the method illustrated in FIG. 2, the defective trace can also be identified by performing two scanning measurements on two layers, with one layer being a layer of the conductive structure and the other layer being a layer of the wafer underneath the conductive structure, as described in the related U.S. patent application Ser. No. 10/090,262, incorporated by reference above.

The method illustrated in FIG. 2 is initially performed on a reference wafer, and any increase in the measured temperature is correlated with the corresponding presence of a defect in the conductive structure, and thereafter the method is repeated for wafers undergoing fabrication.

Specifically, a measurement from a reference wafer and having no defects in the conductive structure is saved, and act 203 is implemented on a wafer under fabrication simply by checking whether the measured intensity of a beam reflected from the corresponding location in the conductive structure is greater than the corresponding measurement on the reference wafer. If so, the wafer is rejected (see act 204) and alternatively the wafer is processed further (see act 205). Therefore, it is not necessary to compute the actual temperature in act 202, although in one variant of act 202 the temperature is determined, and used in the comparison performed in act 203.

In the just-described method, it is necessary to make the measurements at the approximately same relative locations in the conductive structures of the reference wafer and the production wafer to ensure that there is a match when there is no defect. If accurate positioning is difficult for any reason, then a signal obtained by continuous (or periodic) measurement along a length of the conductive structure of a reference wafer is saved and compared with a corresponding signal from the production wafer, as discussed below in reference to branch 207 (FIG. 2).

In one specific implementation, heat is applied to a conductive structure 200 by a laser beam 251 (FIG. 3), and another laser beam 250 is used to measure temperature in the heated region. Depending on the embodiment, the intensity of beam 251 may or may not be modulated. When beam 251 is modulated, the modulation may be at, e.g. a predetermined frequency. In such an embodiment, the reflected portion of probe beam 250 is also modulated at the predetermined frequency, and is detected by use of a lock-in amplifier as described below.

Figure 3:
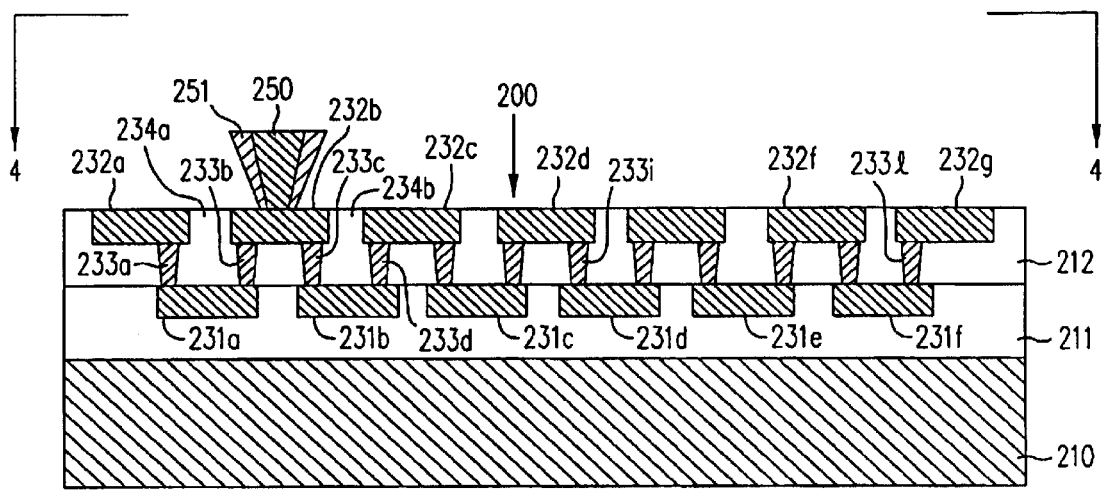
FIG. 3 illustrates, in a cross-sectional view, a multiple level interconnect structure that is evaluated by two coincident laser beams used in accordance with the method of FIG. 2 in one embodiment of the invention.
Figure 4:
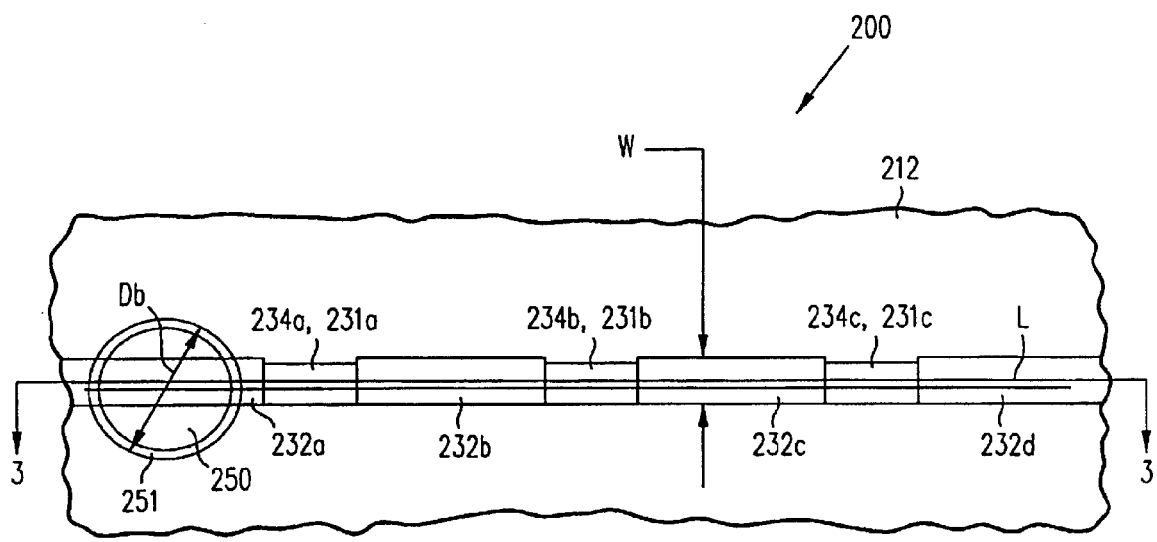
FIG. 4 illustrates, in a plan view (in the direction 4—4 of FIG. 3), the spots formed on a via chain by two coaxial beams used in one embodiment.

In the implementation illustrated in FIG. 3, beams 250 and 251 are coincident (i.e. a spot formed by a smaller diameter beam 250 is completely enclosed within a spot formed by a larger diameter beam 251 as illustrated in FIG. 4). Note that the centers of the two spots need not be identical, and depending on the embodiment the two beams 250 and 251 may be offset from one another, such that they only partially overlap, and in some embodiments spots of the two beams may not even overlap each other.

Although in one embodiment a single measurement at a single site on structure 200 is used to evaluate conductiveness of the structure (e.g. if beams 250 and 251 are repeatably aligned to the same point in each of a number of such structures under production), in another embodiment a number of measurements are made along the length of structure 200, to obtain a sequence of measurements indicative of properties of structure 200 along the length. Specifically, in this embodiment, the above-described acts 201 and 202 are repeated a number of times as illustrated by branch 207 along the length of structure 200, e.g. by moving beams 250 and 251 by a predetermined distance for each measurement.

Figure 5:
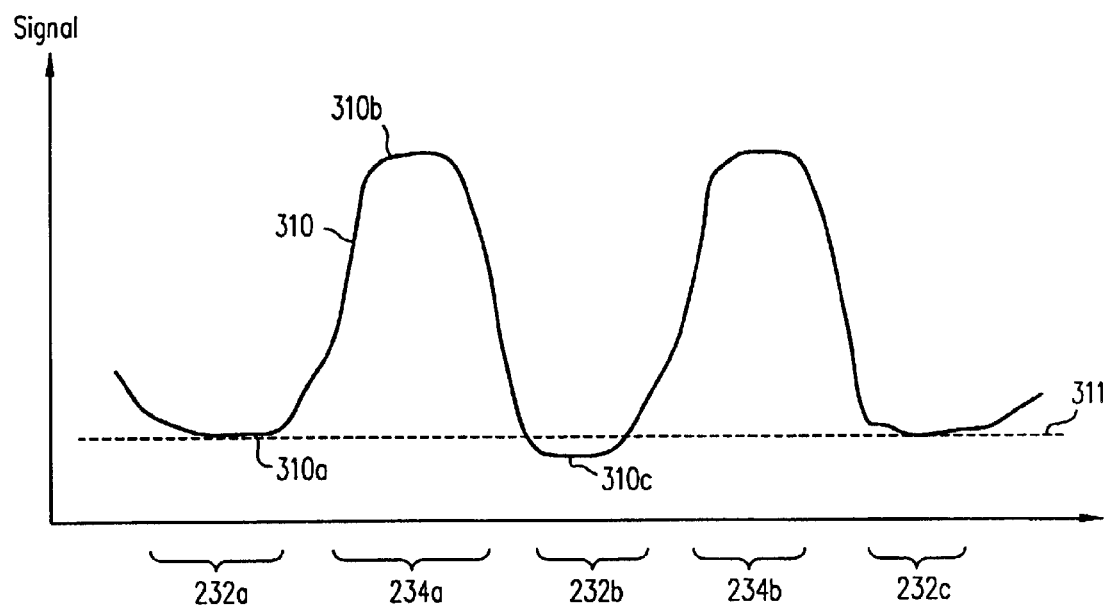
FIG. 5 illustrates, in a graph, a signal measured by the method of FIG. 2 during a scan along the via chain illustrated in FIGS. 3 and 4.
Figure 6:
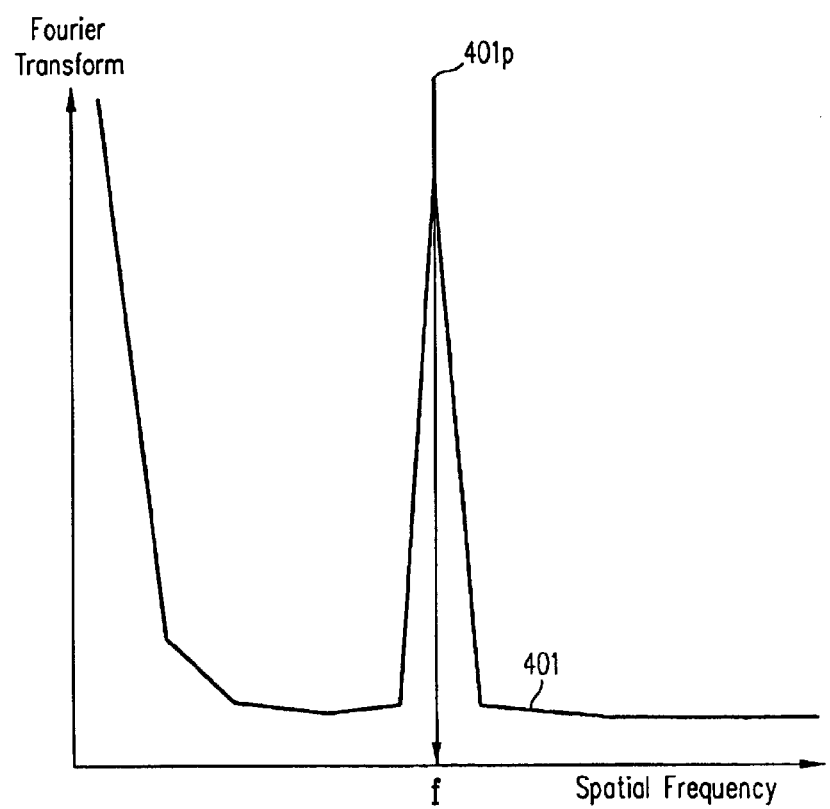
FIG. 6 illustrates, in a graph, Fourier transform of the signal of FIG. 5 plotted along the y axis and the spatial frequency plotted along the x axis.

Scanning of beams 250 and 251 along a line L (FIG. 4) parallel to structure 200 results in the measured signal changing with distance, wherein the signals variation depends on the conductiveness of various elements (such as vias and traces) that form structure 200. Specifically, if vias 233a, 233b, 233c ... 233i ... 233l are arranged periodically in space with a fixed pitch separating two adjacent vias, then the intensity of a signal 310 measured therefrom is periodic as illustrated by FIG. 5. In case of such a periodic structure, a Fourier transform of signal 310, as illustrated by signal 401 (FIG. 6), shows a sharp peak 401P at the spatial frequency f, wherein the spatial frequency f is inversely related to the pitch of the periodic structure 200.

Although a Fourier transform is used in one embodiment to analyze periodic structures, a method of the type described above can also be used with structures that are aperiodic in space. In one embodiment, an aperiodic structure is evaluated by comparing a measured signal therefrom with a corresponding signal from a wafer that is known to be good. Such comparison identifies any defects in a structure formed on a production wafer.

Heat transfer that results in measurement of a periodic signal 310 (FIG. 5) during an act 202 (FIG. 2) may occur as follows. Consider first the case where beams 250 and 251 are scanned over vias 233a–233i (FIG. 3). Beam 251 applies heat to structure 200 as noted above. Reflectance of the metal traces in structure 200 is assumed to be a function of temperature. Therefore, measurement of the reflected portion of probe beam 250 gives a signal that is directly proportional to the temperature in the heated region. Although in one embodiment beams 250 and 251 are coincident as shown in FIG. 4, in other embodiments, beams 250 and 251 need not be perfectly coincident. In some such embodiments, probe beam 250 needs to be over a heated region, and beams 250 and 251 are scanned in unison.

A scan along structure 200, e.g. from left to right along line L (FIG. 4) is done in one embodiment in a series of steps that may be, e.g. smaller than the beam diameter Dp of probe beam 250 as described below in reference to FIG. 15. The shape of a measured signal resulting from scans across via chains provides an unexpected result that can be used to measure via continuity and via uniformity.

As noted above, FIG. 5 shows a representative signal 310 obtained from a scan starting with line segment 232a and ending with line segment 232c of structure 200. The signal 310 has a valley 310a at a line (also called "baseline") 311 when the measurement is made over line segment 232a, due to the dissipation of applied heat into the adjacent segments 232b and 232c because vias 233a, 233b, 233c and 233d (FIG. 3) conduct the applied heat.

When the beams 250 and 251 are over dielectric region 234a however, a large rise in the measured signal is observed. This is because a recessed line segment 231b in metal layer 211, in combination with vias 233c and 233d, acts as a trap for the energy applied by beam 251. More of the incident light from beams 250 and 251 is absorbed in structure 200 during measurement over region 234a, causing a larger signal to be measured as shown by peak 310b (FIG. 5).

Note that at segment 232b the signal 310 has a lower valley 310c than the previously-described valley 310a because of the more uniform presence of vias on both sides of segment 232b (as compared to segment 232a). Thus, the signal 310 (FIG. 5) takes the shape of a sinusoid with a frequency f determined by the spatial periodicity (e.g. pitch p) of the via chain, assuming a fixed rate of movement along line L during the scan.

Note that a periodic signal generated by a structure being evaluated indicates that the structure is not defective (i.e. that the vias are properly connected) regardless of the physical phenomena that may occur during measurement. For example, in different structures, different amounts of light trapping may be present, and even so if the measured signal is in the shape of a sinusoid indicative of the spatial periodicity of the via chain, then it may be concluded that there is no defect in the via chain.

Figure 7:
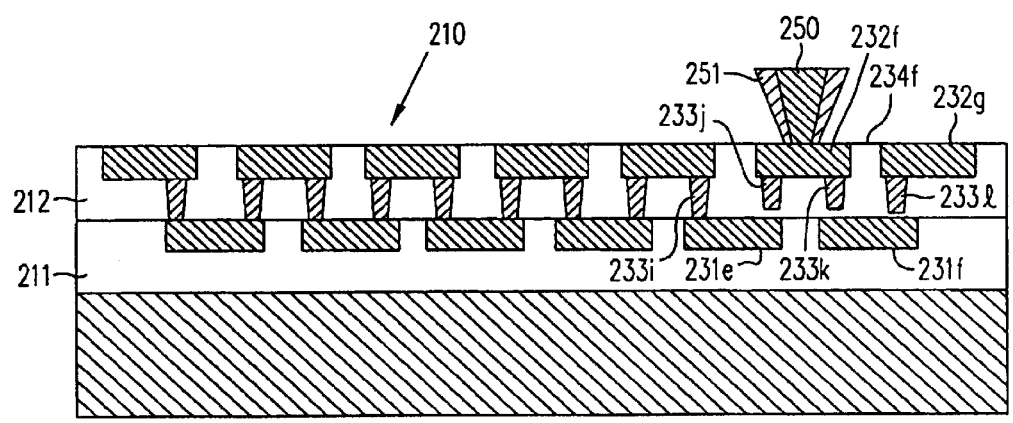
FIG. 7 illustrates, in a cross-sectional view, evaluation by two coaxial beams, of a multiple level interconnect structure with vias 233J, 233K and 233L having defects.

Now consider the method 206 (FIG. 2) performed over a conductive structure 210 (FIG. 7) that has defective vias. Specifically, as illustrated, vias 233j, 233k and 233l are lifted (open), and the line segments 232f and 232g are electrically insulated from line segment 231f in layer 211. Consequently, heat when applied to segments 232f, 231f and 232g cannot flow out of these segments 232f, 231f and 232g.

Figure 8:
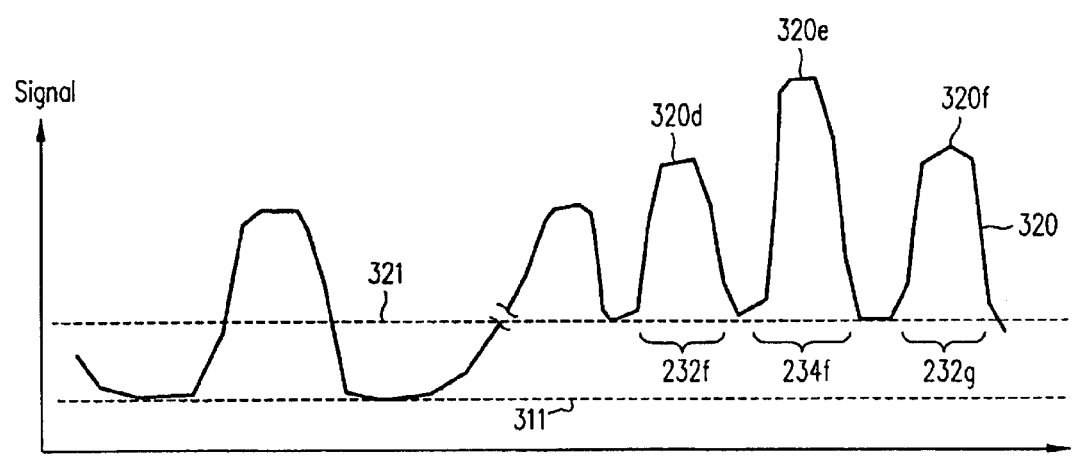
FIG. 8 illustrates, in a graph, a signal similar to the signal of FIG. 5 obtained during a scan along the structure of FIG. 7.

Therefore, the entire baseline is raised to a higher level (from line 311 to line 321 in FIG. 8), and additional peaks occur as beams 250 and 251 scan over segments 232f, 231f and 232g. Specifically, signal peaks 320d and 320f are shown in FIG. 8 as being present over line segments 232f and 232g, in addition to peak 320e over region 234f. Thus the amplitude and frequency profile both change in comparison, at equivalent positions when the vias 233j, 233k and 233l are connected to the line segments 231e and 231f.

The appearance of these additional peaks is an unexpected result, and provides a new tool for analyzing the via continuity, e.g. as described herein. Periodic patterns can be analyzed automatically e.g. by a computer taking the Fourier transform of a signal measured during a line or scan along a via chain. Alternatively, a computer may be programmed to directly compare a measured signal from scanning a via chain under evaluation to a corresponding signal generated by a via chain that is known to be good (e.g. from a reference wafer).

Specifically, in one particular embodiment the computer analyses the Fourier transform to determine the location of one or more local maxima (i.e. peaks). As noted above, in the case of connected vias, a peak $401p$ (FIG. 6) is seen at the fundamental spatial frequency f which is also equal to inverse of the periodicity of the via structure (the pitch frequency of the line segments $232a$–$232g$), and there are small or no peaks at higher harmonics.

For the case of open vias, the computer may be programmed to look for the existence of a peak $402p$ (FIG. 9) in the Fourier transform 402 at twice the fundamental frequency f, equal to twice the inverse of pitch p. In an additional test, the computer may compare the Fourier transform from a via chain under evaluation to the corresponding Fourier transform from a via chain that is known to be good, to find out if any new frequency components are present or if the amplitudes of the frequency components that are normally present have changed.

Figure 9:
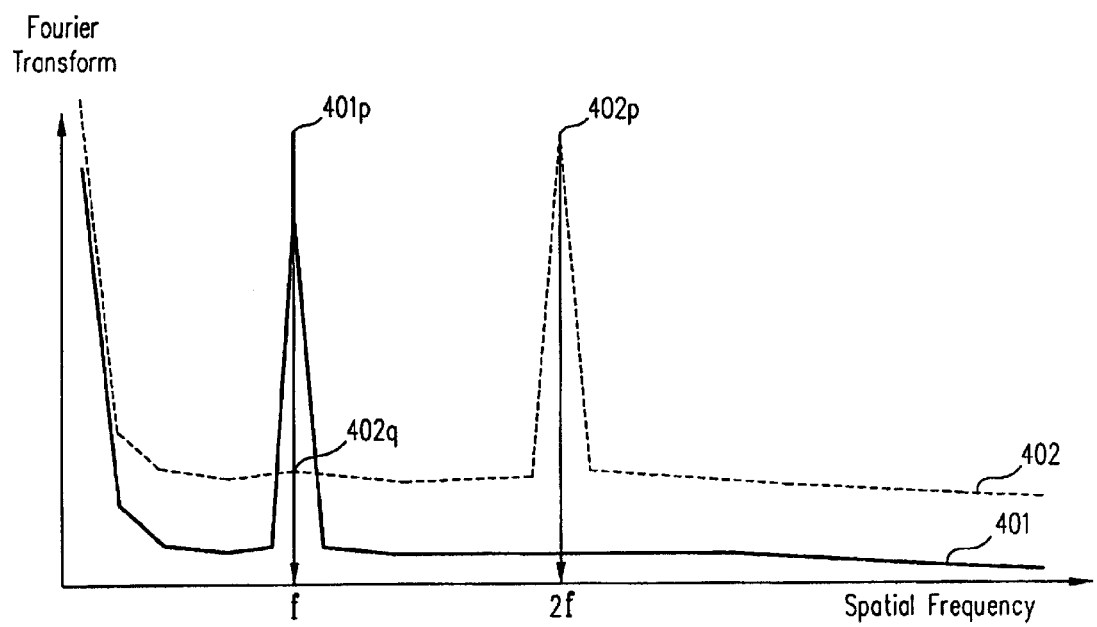
FIG. 9 illustrates, in a graph, similar to FIG. 6, Fourier transform of the signal illustrated in FIG. 8.
Figure 28:
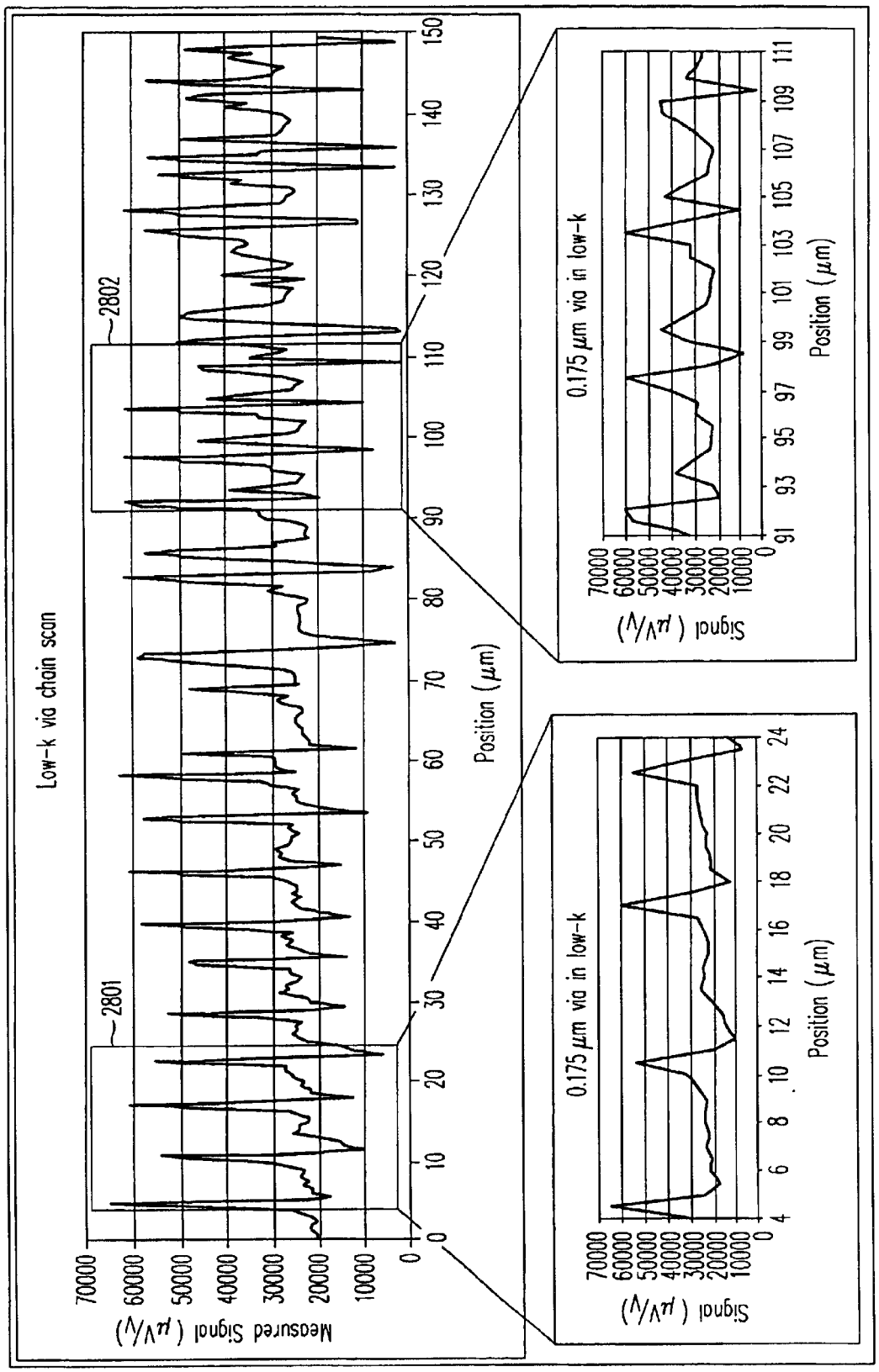
FIG. 28 illustrates, in a graph, the change in a signal indicating a corresponding change in a via chain from good vias to defective vias.

As vias $233a$–$233l$ transition from being connected to being open, the frequency spectrum of the measured signal transitions as well e.g. from transform 401 to transform 402 (FIG. 9). The peak at frequency f disappears when the vias are completely open, so that a perfectly open via chain has only the 2f peak. At intermediate locations wherein both kinds of vias (i.e. good vias and defective vias) are present, both peaks $401p$ and $402p$ may be present and may have different magnitudes. A transition of peaks between frequency f and frequency 2f indicates the degree of connection. Also, open and closed vias may be interspersed through the conductive structure, resulting in a measured signal represented by mixture of the two harmonics $401p$ and $402p$. FIG. 28 is an example of such interspersed good and bad vias.

Scans in different regions of the conductive structure, scans of differing lengths, and analysis of either or both the signal and its Fourier transform may be used to identify the exact condition of the structure, in different embodiments.

A periodic via chain as illustrated in FIG. 3 is only one exemplary class of structures that can be evaluated as described herein. Other conductive structures can be evaluated in a similar manner. For example, a number of vias may connect between continuous lines rather than segments. The segments may not be located in a periodic manner (as noted elsewhere herein). Also, connections could be between two co-planar lines (in a single metal layer) rather than from metal 1 to metal 2. All of these cases would allow use of an evaluation method of the type described herein. Scans of different structures would have different frequency components. However, changes in the quality of via connections would change the frequency spectrum and the shape of the scan response curves.

Figure 10:
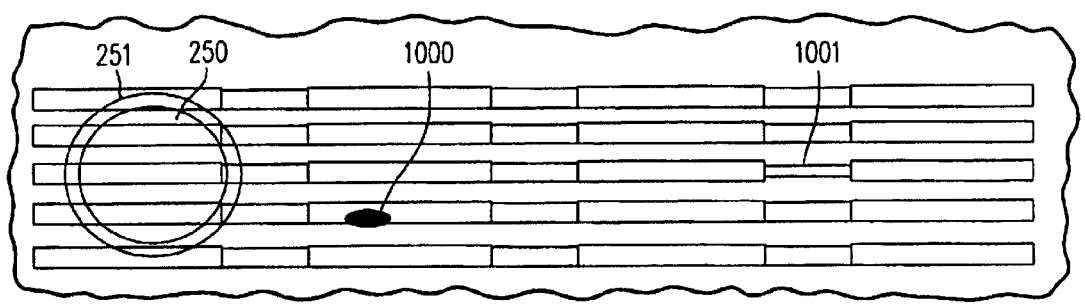
FIG. 10 illustrates, in a plan view, evaluation of a group of via chains by the method of FIG. 2 in another embodiment.

As illustrated in FIG. 10, beams 250 and 251 may be of diameters so large as to simultaneously cover a number of via chain structures $200a$–$200r$, depending on the embodiment. In such a case, if there is a defect, it may not be necessary to determine which of structures $200a$–$200r$ is defective, because the wafer as a whole is simply rejected (i.e. not processed any further).

In one embodiment heating beam 251 is slightly larger in diameter than measurement beam 250, so that the measurement is performed in a region of structure 200 that is substantially constant in temperature (over time), assuming that beam 251 applies heat at a constant rate. As noted above, if the amount of applied heat changes over time, e.g. at a fixed frequency, then the measured signal may be temporally correlated to the applied heat amount e.g. at the fixed frequency.

Specifically, in some embodiments of the type described herein, a heating beam 251 can be used as described in U.S. patent application Ser. No. 09/095,805 which issued as U.S. Pat. No. 6,054,868. Such a heating beam 251 has a power (also called "heating power") modulated at a frequency that is selected to be sufficiently small to cause at least a portion of the heat (e.g. a majority in some embodiments, although just 10% may be sufficient in other embodiments) to transfer by diffusion from the point of heat application. In one example, the heating beam 251 has a wavelength of 0.83 microns, has an average power of 10 milliwatts, a diameter of 2 microns and is modulated at 2000 Hertz.

The modulation frequency of heating beam 251 is selected to be sufficiently small to ensure that at any time the temperature of the conductive structure is approximately equal to (e.g., within 90% of) the temperature of the conductive structure when heated by an un-modulated beam (i.e., a beam having constant power, equal to the instantaneous power of the modulated beam). For example, the modulation can be sinusoidal between 0 and 50 milliwatts, i.e., P=50 sin ($2\pi$ft), where f is the modulation frequency. In such an example, at the time when the modulated power has an instantaneous value of 25 mW, the temperature under the heating beam approximately equals (e.g., is no less than 90% of) the temperature obtained with a heating beam having constant power, e.g., 25 mW.

In one embodiment, the modulation frequency is selected to cause a number of traces in the conductive structure illuminated by the heating beam 251 to be at substantially the same temperature relative to one another (e.g., varying less than 10% between adjacent traces). Such a linear response condition occurs when the thermal wavelength $\lambda$ (which is the wavelength of a thermal wave that is formed in the structure) is at least an order of magnitude larger than the diameter of the illuminated region.

Therefore, when a heating beam 251 is modulated, the temperature T (and therefore the reflectance) of the conductive structure is also modulated in phase with modulation of the heating beam (under linear response conditions). As noted above, the reflected portion of a probe beam 250 (which is sensed to generate an electrical signal) is also modulated, in phase with modulation of the heating beam 251. The modulated electrical signal is detected by use of a lock-in amplifier as stated in the U.S. Pat. No. 6,054,868. The modulated electrical signal can be used to identify defects, such as voids in vias. As noted elsewhere, a heating beam and a probe beam can be offset from one another, even in embodiments where modulation is used. The distance of separation between the point of heat application and the point of measurement can be as large as, for example, 5–8 $\mu$m because the effect of applied heat (the linear thermal response) is noticeable for a greater distance (e.g., 10–15 $\mu$m) before reaching room temperature.

A via chain in conductive structure 200 may include line segments $232a$ ... $232g$ and $231a$ ... $231g$ and vias $233a$ ... $233l$. The width W (FIG. 4) of structure 200 may or may not be larger than the diameter Dp of probe beam 250. In one embodiment, it is only necessary for the via chain in structure 200 to intercept light from the beams 250 and 251. Typical dimensions are as follows for such a via chain: line segment length of 5 $\mu$m, via diameter of 0.25 $\mu$m, line segment width W of 0.25 μm, and the diameters of 1.5 and 1.0 μm for the heating beam 251 and probe beam 250 respectively. Note, however, that the diameters of beams 250 and 251 can be smaller than line segment width W and also smaller than the via diameter, in other embodiments.

When the intensity of heating beam 251 is modulated and a lock-in amplifier is used to measure the variation in reflection of probe beam 250 at the modulation frequency, the temperature rise of conductive structure 200 is determined in one embodiment, for different modulation frequencies. The temperature rise and reflectivity are both functions of modulation frequency, also called frequency response signal (see FIG. 11B). This signal is measured and its amplitude changes depending on the presence of defects in structure 200. The measured amplitude is used in one embodiment to accept or reject wafers.

Figure 11A:
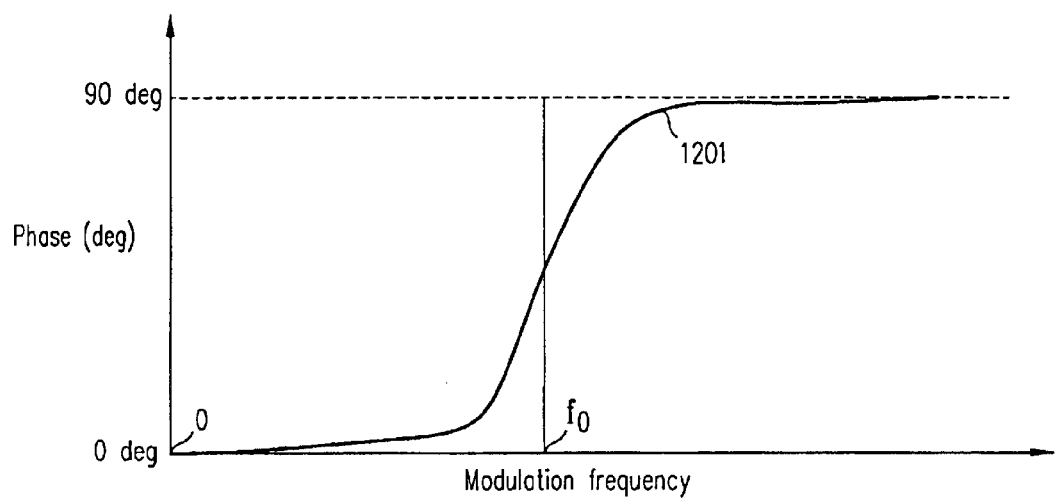
FIG. 11A illustrates, in a graph, loss of in phase response of a conductive structure in response to increasing modulation frequency.

Specifically, at a low modulation frequency, e.g. less than 1 KHz, structure 200 heats and cools in phase with the applied heat shown to the left of frequency $f_o$ in FIG. 11A. At a high modulation frequency (greater than $f_o$), the vias 233a–233l in structure 200 are less able to respond in phase (i.e. the vias cannot dissipate heat fast enough to remain in phase with the changing intensity of heating beam 251). An upper limit on the modulation frequency at which vias are able to respond in phase depends on the dimensions of the vias. For example, a copper via plug of 0.2 mm diameter and 1 mm length has a 3 dB (50%) point at one 1 MHz. A more massive structure, such as a via connected to a line segment that is part of a via chain, would have a lower roll-off frequency, and 1 MHz would in this case be a high modulation frequency.

Figure 11B:
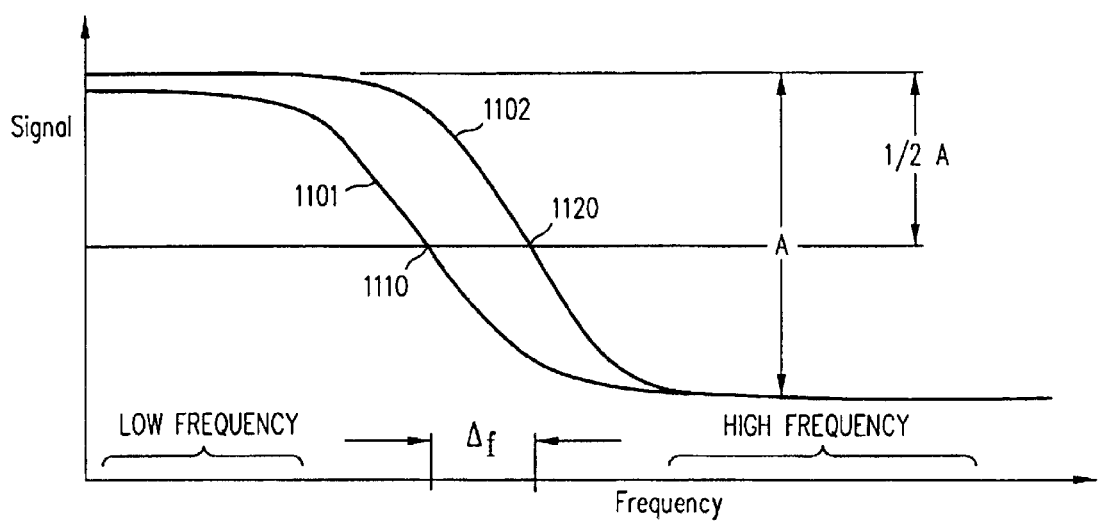
FIG. 11B illustrates, in a graph, the frequency responses of good and bad via chains measured in accordance with the method of FIG. 2.

The frequency response signal therefore drops with increasing frequency, as illustrated by signal 1101 plotted in FIG. 11B. A partially filled via (i.e. a via that is defective) has a smaller thermal mass and therefore is able to remain in phase with intensity of heating beam 251 better than a completely filled via (i.e. a good via), and therefore the corresponding frequency response signal 1102 is shifted to a higher frequency, as illustrated in FIG. 11B. Similarly, a via connected to a metal line has a higher thermal mass than a disconnected via, and responds at a lower frequency, as compared to a disconnected via, which would respond at a relatively higher frequency.

Such a shift in the frequency response signal may be detected by a computer, which is programmed in one embodiment to perform the following acts. Specifically, intensity of the reflected portion of probe beam 250 is measured as a function of frequency of modulation. Next the frequency at which the measured signal falls to 50% of its maximum value (which is the value at zero frequency) is identified, e.g. to be at point 1120 for signal 1102 (FIG. 11B). This identified frequency is compared to a predetermined limit (which may be set at point 1110, for example, by performing the same acts on a via chain structure that is known to be good). If the difference Δf is significant (e.g. greater than 10%) then the via chain structure under measurement is deemed to be defective and the wafer is rejected.

Although in one embodiment, the frequency is measured as described above, in another embodiment a phase difference between modulation of heating beam 251 and modulation of a reflected portion of probe beam 250 is measured. This phase difference measurement is used in act 203 (FIG. 2) to identify an irregularity in the conductive structure being evaluated. Specifically, when the structure has a defective via, the measured phase difference is larger than the phase difference detected with a conductive structure that has good vias (see FIGS. 11A and 11B), and this change in phase difference is used to evaluate the quality of vias for the following reason.

When the intensity of a beam 251 generated by the heating laser is modulated sufficiently slowly (i.e. at a low frequency, e.g. <1 KHz), the temperature of the via(s) stays in phase with the heating beam modulation. However, when the intensity of heating beam 251 is rapidly modulated (e.g. >1 MHz), the temperature of the vias goes out of phase, because the vias cannot heat and cool sufficiently fast. Therefore, in such an embodiment of using modulation, the frequency of the heating laser's modulation is changed, and the phase of the reflected portion of the probe beam 250 is measured.

Hence, in some modulated beam embodiments, a first laser heats one or more vias, while a second laser reflects from the vias, and intensity of the reflected portion is used to evaluate the vias. Specifically, the first laser is modulated at a variable frequency. The reflection of the second laser contains a modulation component because reflectance of the via is a function of its temperature. The phase difference between the heating laser modulation and the reflected modulation component is measured with a lock-in amplifier, as the frequency of modulation is swept from a low frequency to a high frequency. Changes in the curve of phase shift vs. frequency are then used to indicate changes in the structure related to problems such as voiding, disconnection or under-filling.

Figure 12:
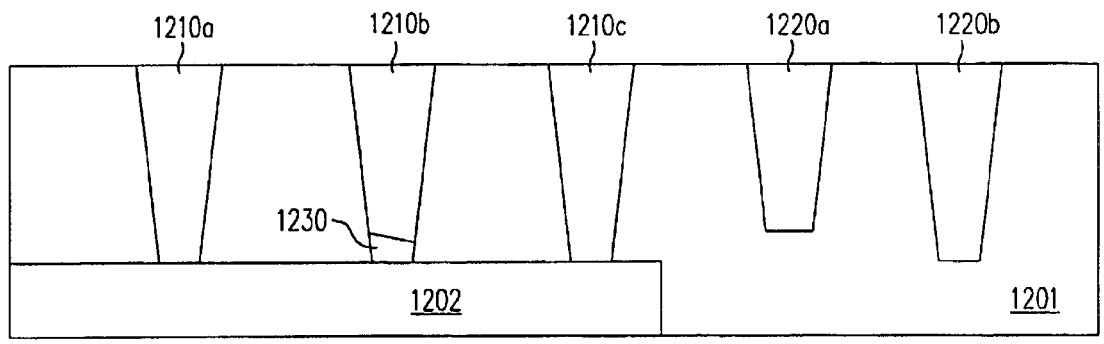
FIG. 12 illustrates a multiple level interconnect structure having a dielectric layer as the uppermost layer, and more than two conductive layers being evaluated using the method of FIG. 2.

Consider, for example, structure 1201 (FIG. 12), which consists of metal line 1202 and vias 1210a–1210c and 1220a and 1220b. The background material is an insulator, such as silicon dioxide. The vias in structure 1201 are formed in holes etched in the insulator and back-filled with metal. Vias 1210a–1210c are connected to metal line 1202. However, void 1230 prevents via 1210b from connecting.

Figure 13:
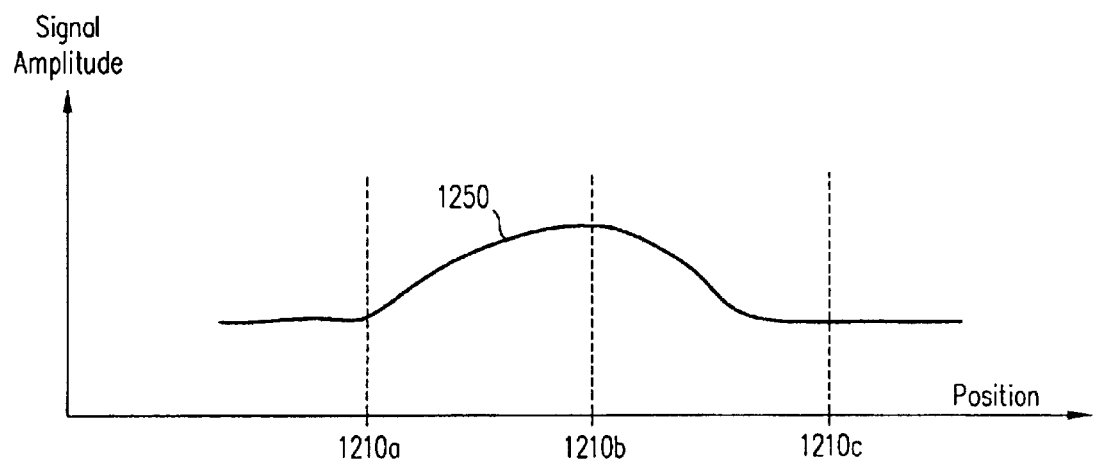
FIGS. 13 and 14 illustrate, in graphs, the signal and phase at a constant frequency, as a function of distance along the length of a via chain of the type illustrated in FIG. 12.

When all three vias 1210A, 1210B and 1210C are heated during a scan of the type described herein, the resulting signal 1250 shows that the grounded vias 1210A and 1210C are able to more quickly and easily dissipate the heat than via 1210B that is open (see FIG. 13). Signal 1250 (FIG. 13) is an illustration of the amplitude response from via chain 1201 at a constant frequency, as a function of distance along the structure 1201. As seen from FIG. 12, via 1210B has a smaller thermal mass than vias 1210A and 1210C, and consequently via 1210B heats up to a higher temperature than vias 1210A and 1210C. The higher temperature of via 1210B is illustrated by the local maxima in signal 1250 (FIG. 13).

Figure 14:
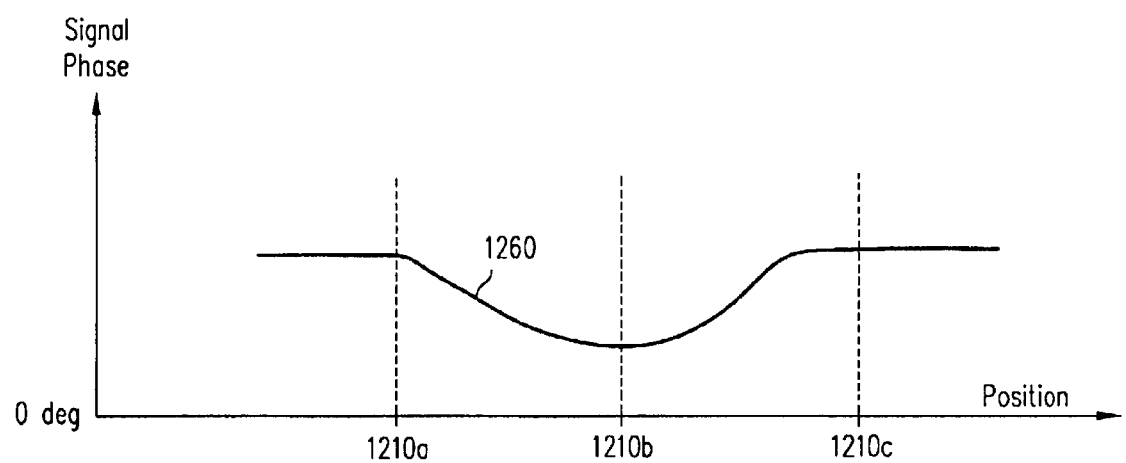

Similarly, vias 1210a and 1210c that are grounded to metal line 1202 respond more rapidly to heating and cooling and their temperature stays in phase at a higher heating modulation frequency as illustrated by the phase response signal 1260 (FIG. 14). Via 1210b, which is not thermally grounded does not respond in phase with modulation of the applied heat.

In the case of two unconnected vias 1220a and 1220b (FIG. 12), via 1220a has a smaller thermal mass, since it is under-filled. Therefore, open via 1220a responds in phase until a higher modulation frequency than open via 1220b.

Figure 15:
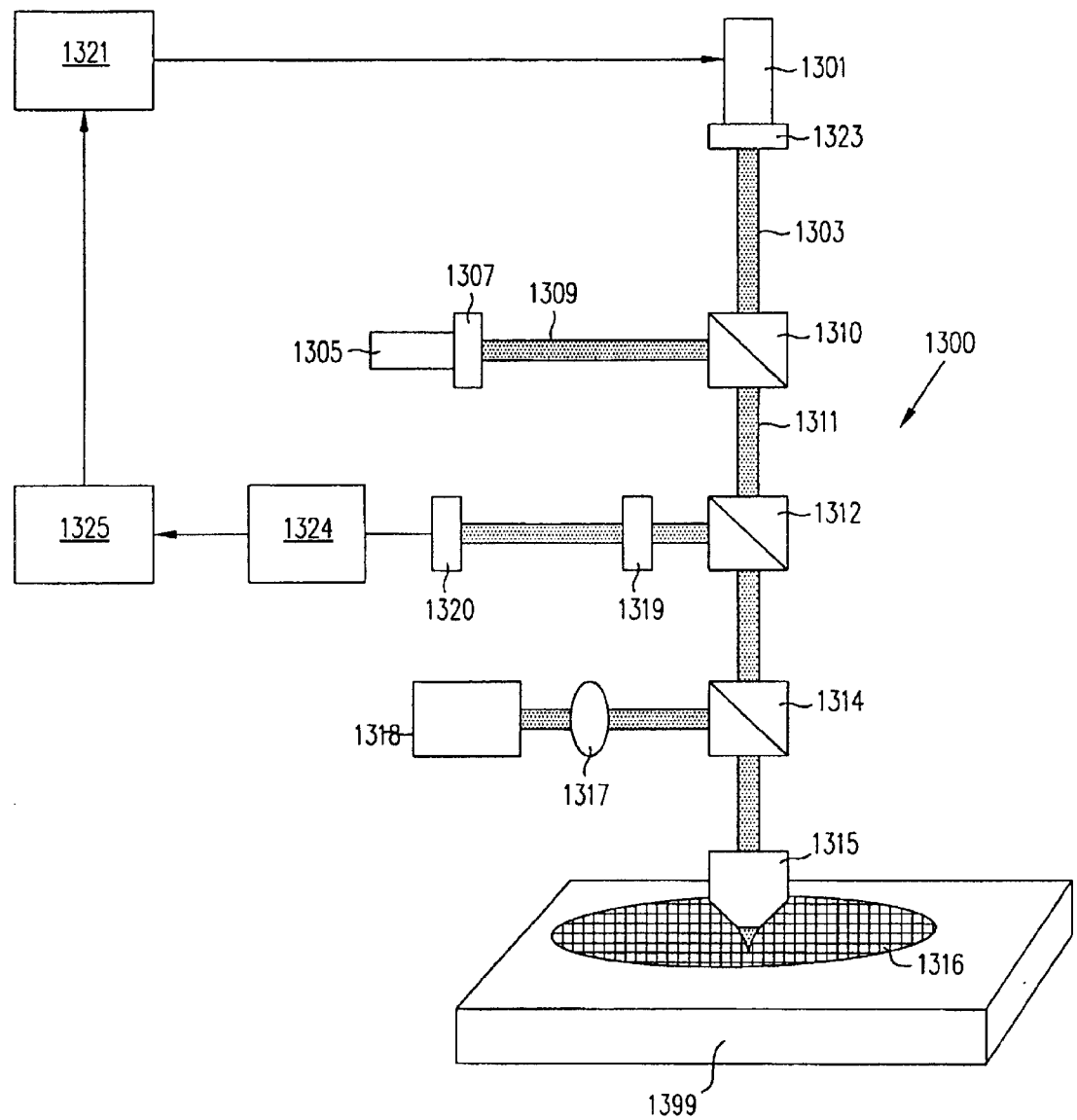
FIG. 15 illustrates, in a block diagram, an apparatus used with the method of FIG. 1 in one specific implementation.

FIG. 15 shows a representative measurement apparatus 1300 using a laser 1301 to heat the conductive structure in wafer 1316 and a second laser 1305 to measure temperature of the heated region. However, alternate apparatuses are equally viable. For example, an electron or ion beam can be used to heat a conductive structure in wafer 1316 and an infrared camera or detector (e.g. thermal imaging detector)

can be used to measure the blackbody temperature of the conductive structure.

Furthermore, in yet another embodiment, the temperature is measured at a fixed distance from the point of application of heat. In such an embodiment, contact probes may be used to apply heat and to measure temperature. Note however that use of such contact probes while effective in obtaining a measurement as described herein have the drawback of introducing defects during manufacture of integrated circuit dies on the wafer, simply due to making contact.

In one specific embodiment of apparatus 1300, laser 1301 is a diode laser (e.g. made by Spectra Diode Labs of San Jose, Calif.), emitting a beam of intensity 100 mW at a wavelength of 830 nm. A laser driver 1321 (e.g. Part number 8000 OOPT-42-12-02-NN available from Newport Corporation, Irvine, Calif.) provides a sinusoidal signal to laser 1301, thereby to modulate the intensity of a heating beam generated therefrom. Optics 1323 (e.g. Part number C390TM-B, Thor Labs, Newton, N.J.) collimate the output of laser 1301, creating beam 1303.

In one embodiment, heating beam 1303 is unpolarized, while in another embodiment, heating beam 1303 is polarized. Specifically, in certain embodiments, when the line width is less than 0.2 mm, heating beam 1303 is polarized. The polarization direction is oriented parallel to the length of a via chain in structure 200, to increase heat absorption, e.g. due to interaction between heating beam 1303 and the metal line segments (also called traces) in structure 200.

As noted elsewhere herein, certain embodiments use one or more polarized beams when the line width is less than the wavelength. In such embodiments, light polarized parallel to a line (also called "trace") has a larger interaction cross-section than light polarized perpendicular to the line. Use of one or more parallel polarized beams (either as a heating beam or as a probe beam or both beams may be polarized) increases the efficiency of evaluating structure 200 and therefore increases the signal-to-noise ratio (SNR) of the measured signal.

Laser 1305 which is also included in apparatus 1300 as one embodiment may be made by Spectra Diode Labs, and emits a beam of intensity 50 mW at a wavelength of 980 nm. Laser 1305 generates probe beam 1309 at a constant intensity. Depending on the embodiment, probe beam 1309 may also be polarized, parallel to the length of the via chain. Optics 1307 (e.g. Part number F230FC-B, Thor Labs, Newton, N.J.) collimate the output of laser 1305 to create probe beam 1309.

Apparatus 1300 also includes a dichroic mirror 1310 (e.g. Part number O5BR08 available from Newport Corp.) that transmits light from laser 1301 and reflects light from laser 1305 (which is of longer wavelength than light from 1301). Dichroic mirror 1310 combines beams 1303 and 1309, providing single combined beam 1311. Combined beam 1311 passes through various optics and is ultimately focused on wafer 1316 with objective lens 1315, which is e.g. a 100×0.9 NA lens (such as Part number 1-LM5951) from Olympus of Tokyo, Japan.

The beams reflected by wafer 1316 pass back to a 50:50 beam splitter 1312, which diverts 50% of the return beams toward detector 1320 (such as silicon PIN photodiode, e.g. Part number S2386-8K from Hamamatsu Corporation, Bridgewater, N.J.) through filter 1319. Filter 1319, which may be a GaAs wafer, removes the reflected portion of light from heating beam 1303, so that the detector sees only light from probe beam 1309. Trans-impedance amplifier 1324 converts an electrical signal output by detector 1320 to a voltage, which is measured using a lock-in amplifier 1325 (such as SDP lock-in amplifier, e.g. Part number 7265 available from EG&G Instruments, Atlanta, Ga.). Lock-in amplifier 1325 has an oscillator that is also used to drive the modulation of laser driver 1321. The oscillator is operated at a frequency on the order of 2 kHz or lower.

In one embodiment, the oscillator frequency is selected to be sufficiently low to prevent generation of a thermal wave, allowing the temperature distribution in a via chain structure at any instant (e.g. over the duration of a single cycle of modulation, e.g. over 500 $\mu$sec for 2 KHz modulation) to approximate the instantaneous temperature that would be normally seen in steady state (e.g. linear response conditions as discussed above, in relation to U.S. Pat. No. 6,054,868 which has been incorporated by reference).

In other embodiments, the modulation frequency may be selected to be large enough to cause a portion of the energy from heating beam 1303 to be converted into a thermal wave, while the remaining energy of beam 1303 is sufficient to cause the reflected portion of probe beam 1309 to be modulated at the modulation frequency when a via chain (or other feature is being evaluated) in structure 200 is not defective. Therefore, a method of the type illustrated in FIG. 2 is used in accordance with the invention to further process a wafer if the measured signal is within a predetermined range of a corresponding signal from a reference wafer (regardless of the presence or absence of a thermal wave depending on the embodiment).

Regardless of the frequency selected, the use of a modulated heating beam as described herein enables use of a lock-in amplifier to obtain a very sensitive measurement of small temperature changes. Note, however, that in other embodiments, the heating beam 1303 may be of constant intensity (i.e. no modulation) as long as the reflectance of the conductive structure is measured with sufficient accuracy (e.g. 1%). A thermal imager may be used instead of detector 1320, to perform such a constant intensity measurement.

It is well known that the reflectance of a metal is a function of temperature. Cu, for example, has a coefficient of reflectance change of $-1.55 \times 10-5/°$ C. (about 15 parts per million). As noted above, the reflectance of the conductive structure that is being heated by a modulated heating beam 1303 will cycle approximately in phase with modulation of the heating beam 1303. Specifically, the phase depends on the conductive material used to form the structure, e.g. since the reflectance of copper decreases with increasing temperature, the reflected signal will be approximately 180 degrees out of phase for this metal, depending on the amplitude of variation in temperature.

Note, however, that the amount of phase change depends on the composition of the conductive material that is used to form vias and traces in the conductive structure (in addition to depending on the change in temperature). The amount of heat being applied may be selected to ensure that the changing reflectance of the conductive structure due to temperature change causes a modulation signal in the reflected portion of the probe beam 1309 (e.g. in embodiments that modulate the intensity and/or the polarization of a heating beam). This is the signal measured by the lock-in amplifier 1325. The intensity of the measured signal is therefore a function of the temperature of the via chain at the measurement point.

The apparatus 1300 illustrated in FIG. 15 also includes a vision system to enable location of the laser beams 1303 and 1309 on the via chain in structure 200 in wafer 1316. Beam splitter 1314 diverts approximately 10% of the reflected light to lens 1317 and camera 1318. In this embodiment, objective lens 1315 and lens 1317 form a microscope with a magnification of approximately 1000×. Camera 1318 of apparatus 1300 is connected to an external vision system (e.g. Patmax for Cognex, Inc. of Boston, Mass.). The vision system in turn is connected to a wafer stage 1399 in apparatus 1300 to enable automatic alignment of the laser beams 1303 and 1309 to the via chain structure 200. Apparatus 1300 also includes a white-light illuminator (not shown) to provide illumination for the vision system.

Figure 16:
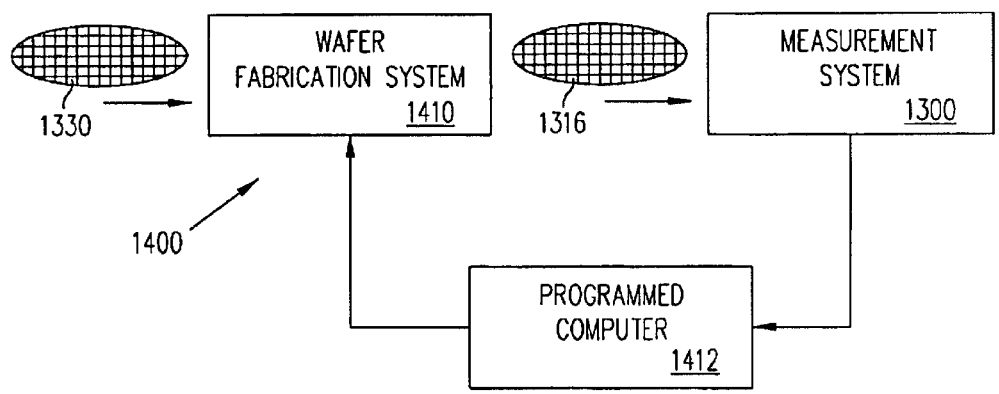
FIG. 16 illustrates, in a high level block diagram, use of the apparatus of FIG. 13 in an in-line manner during fabrication of wafers, for use in process control in one embodiment of the invention.

FIG. 16 shows one specific application of apparatus 1300 illustrated in FIG. 15. In one example, wafer 1330 is in production and requires a level of metal interconnection (also called interconnect layer). During the fabrication process, wafer 1330 is transferred into process module 1410, where the just-described interconnect layer is formed thereon (and this wafer is now labeled as 1316 and is to be evaluated).

Module 1410 may create one or more voids when creating the interconnect layer in wafer 1316, depending on the process being used. For example, electroplated copper is the metal of choice for dual damascene interconnect devices. However, the process of creating copper metal trenches and vias leaves the conductive structures being formed vulnerable to voids.

After the diffusion barrier (typically Ta or TaN) is deposited, a thin copper seed is deposited by physical vapor deposition (PVD) to ensure equal potential across all features for electron transfer between the plating bath used to deposit the electroplated copper. If the PVD copper seed layer is too thin or does not cover all the features in trenches or vias, electroplated copper will preferentially plate on areas covered with copper, resulting in no deposition, or voids, on the areas with little or no copper seed.

Because of the line-of-sight nature of PVD, narrow device features that have high aspect ratios are prone to little or no copper seed deposition on the sidewalls near the bottom of the features, which results in "bottom" voids. Any "shadowing" feature in a trench or via that blocks the PVD line-of-sight will result in lack of copper seed coverage, also resulting in a void.

A non-optimized concentration of accelerator in the plating solution can lead to "seam" voids in a conductive structure and such voids can be detected by the method of FIG. 2. The correct concentration of accelerator species in the bottom of trenches and vias enhances "bottom up" electroplated copper fill. If the concentration of accelerator in the plating solution is too low or too high, the deposition rate in the bottom of the features approaches that of the sidewalls and top, resulting in conformal copper deposition. This conformal deposition coupled with non-conformal cusping of PVD coverage at the top of device features forces closure of the top of the feature before trenches or vias are completely filled, resulting in a seam void.

There are several other mechanisms for void creation, such as poor adhesion of a via copper plug or trench copper line to the underlying barrier metal, void agglomeration due to copper recrystallization, and electromigration. Voids created by any of these mechanisms are detected by the method of FIG. 2.

The method of FIG. 2 also detects other defects, such as a poor connection at the bottom of a via, or poor plating that may be caused by, for example, presence of residue from an etch process used to etch a hole in the dielectric layer in which a via is formed. In the just-described example, instead of residue, the etch process may be incomplete and therefore cause poor connection or poor plating at the bottom of the via.

In addition, an integrated circuit contains several interconnect layers. Formation of such a layer of an integrated circuit requires exposure to temperatures of several hundred degrees Centigrade during the deposition of the dielectric layer. Exposure to such high temperatures can cause an otherwise good via to pull back (either partially or completely) at the bottom of the via hole, resulting in a partial or open connection with the underlying trace. Also, etch residues can corrode the connection at the bottom of the via during such high-temperature exposure. These types of voids are buried, and hence invisible from the top of the integrated circuit. In addition, the voided or partially filled vias are buried under dielectric layers. Thus, a method of the type described above in reference to FIG. 2 is particularly advantageous in such a situation because the method measures degree of voiding, as opposed to just identifying whether a via is connected or open. Moreover, a method in accordance with the invention can be used after transparent dielectric layers have been applied to bury the via structures.

Wafer 1316, with a completed interconnect layer, possibly having one or more voids, is measured in system 1300 to determine if vias have been successfully formed. Measurement can be in selected areas of the active device pattern, or in a test structure adjacent to the active device pattern. Measurement signals generated by system 1310 are transferred to a computer 1412. In the event that results are judged unacceptable (for example, because a strong second harmonic signal is detected), signals are sent by computer 1412 to process module 1310 to alter the process to enable correction of the detected problem. Alternatively, computer 1412 may simply cause the process module 1410 to halt, thereby to prevent production of additional defective wafers. A human operator may restart module 1410 after correcting a via voiding problem.

Figure 17:
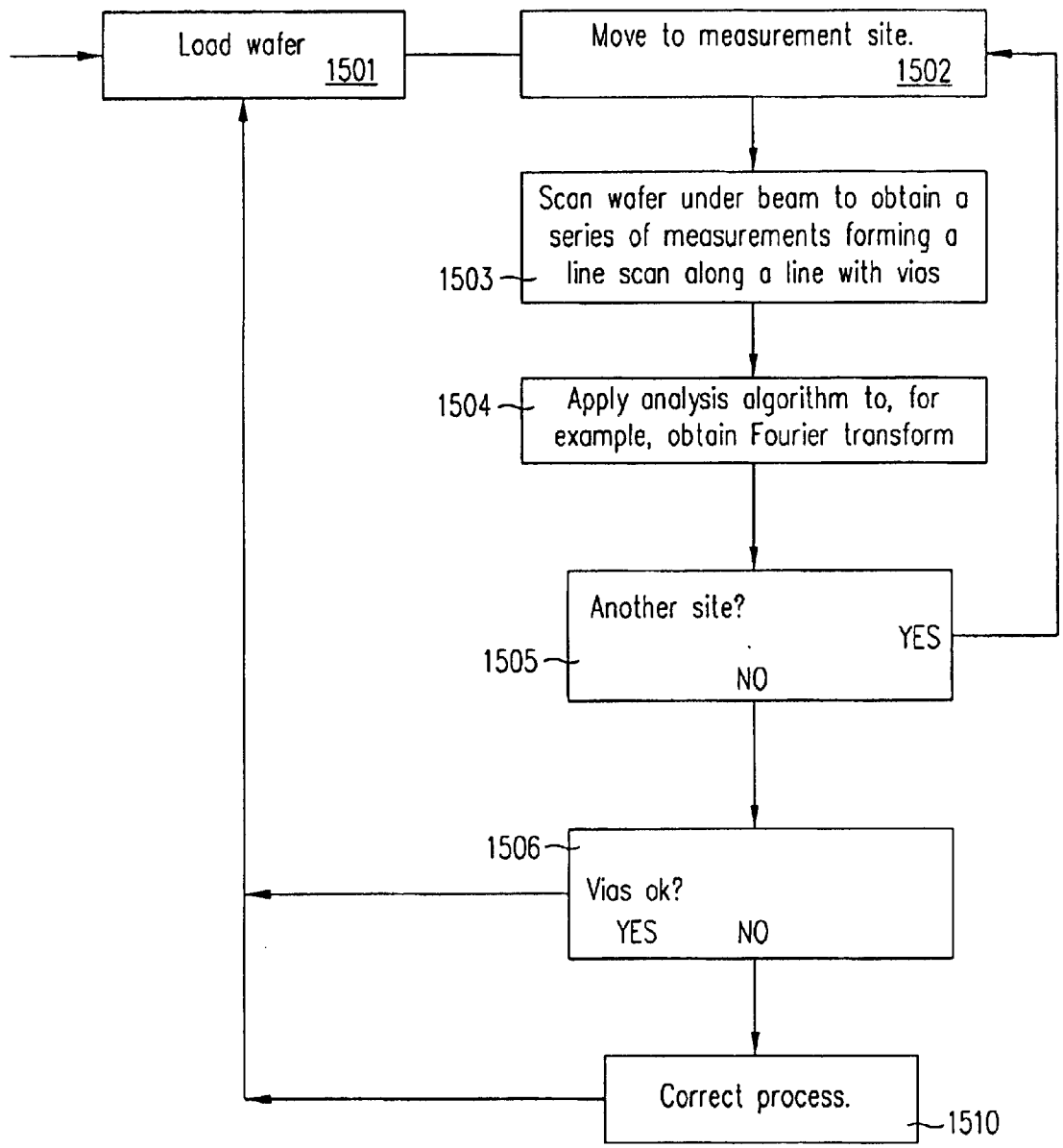
FIG. 17 illustrates, in a flowchart, acts performed by the system of FIG. 14 in one embodiment.

FIG. 17 shows a flow chart associated with measurements that are performed by apparatus 1300 in one specific embodiment. In act 1501 a wafer 1316 is loaded into the measurement system 1300 (FIG. 15). In act 1502 the wafer 1316 is moved to a position so that a scan can be made along a via chain (this position is also called the measurement site). The beams 1303 and 1309 are both focused onto the measurement site during act 1502.

A loop of acts 1503–1505 is now entered to perform measurements. A line scan along the conductive structure (such as the via chain) is performed in act 1503 as described briefly above in reference to FIG. 4. Specifically, the line scan consists of a sequence of taking a measurement, translating the wafer a small distance typically along a straight line (in one example less than the diameter of probe beam 1309) so that the feature under measurement is translated under the beam and a new measurement site is illuminated by beam 1309, taking a measurement at the new measurement site, and repeating these acts. As described earlier, the scan may be stopped periodically to verify that the beam is properly positioned on the via chain and to adjust the positioning as required.

In one embodiment, the measurement sites are evenly spaced by a distance smaller than the beam diameter. For example, steps of 0.25 $\mu$m may be made with probe beam of diameter 2 $\mu$m. In one specific implementation of such a scan, the stepping distance is less than the beam diameter, in order to provide a plot of a continuous signal from the scan. In another embodiment, the location of each via is a measurement site, although one or more non-via locations between two vias may also be used as measurement sites.

In another embodiment, a stage on which the semiconductor wafer is normally placed is set in free motion, moving at a speed of 2 micrometers per second, and the measurement signal is read continuously and stored. This embodiment provides an analog signal equivalent to a series of measurements made by stepping and measuring as described above. This embodiment obtains a greater noise in the measurement, because of the motion of the stage, and because of the shorter duration of the lock-in integration time, but improves the throughput of the measurement method substantially. Therefore, scanning as described herein covers both, the free motion embodiment (in which an analog signal is measured continuously) as well as the above-described stepping embodiment (also called "hopping embodiment") in which a series of individual measurements are made.

For example, beams 250 and 251 are placed initially over a first via 233a (FIG. 3) and a measurement is taken. The semiconductor wafer containing structure 200 is then stepped e.g. by 0.25 $\mu$m and a second measurement taken. The just-described acts are repeated until a scan along a representative length of a via chain is made, for example.

In step 1504 the set of measurement signals is analyzed, for example, by taking the Fourier transform of a curve defined by the set of measurement signals (which have discrete values, one for each measurement site or, alternatively, with a continuous scan each value output by the lock and amplifier during a scan). In another embodiment, the scan is compared to a scan (also called "reference scan") from a reference wafer containing a via chain known to be good. Deviation in features (such as a peak amplitude greater than a set value), beyond said limits result in rejection of the wafer under production as being bad, in step 1506.

In one embodiment, the Fourier transform data is then stored for later use in accepting or rejecting the wafer. In act 1505 a decision is made as to whether another conductive structure on wafer 1316 is to be evaluated. If so, acts 1502–1504 are repeated, e.g. until all conductive structures on wafer 1316 have been evaluated. Depending on the embodiment, only selected conductive structures may be evaluated.

In act 1506 the stored data are analyzed to determine if vias in the via chains being evaluated are acceptable, or if there is a problem. If they are acceptable, the current wafer is processed further in the normal manner and a next wafer is loaded for evaluation. If they are unacceptable, the problem is reported for corrective action and the interconnect creation process in module 1410 (FIG. 16) is halted.

As noted above, apparatus 1300 of one embodiment is a two-laser system, performing a quasi-static measurement. A red laser (830 nm wavelength) pumps heat into the metal lines in the wafer under evaluation. A second laser (980 nm wavelength) measures reflectance at the heated spot to deduce temperature changes. The lasers are chosen for reasons of lifetime, and are rated for 100,000 hours of tool operation. As noted elsewhere herein, an external vision system, such as a Cognex PatMax vision system is used to find measurement sites in one embodiment.

Apparatus 1300 of one embodiment measures metal reflectance changes due to temperature changes induced by heating with a 2 $\mu$m diameter laser spot formed on the wafer being evaluated. The temperature rise, typically in the range of 10 to 40° C., correlates to the resistance/length for traces, and sheet resistance for pads. The measured signal generally increases with decreasing line cross-section area, enabling measurement of individual lines and line arrays of width <0.12 $\mu$m. As noted above, good vias shunt heat, and voids restrict heat flow, providing the measured signal with sensitivity to via continuity and line voiding.

Voids were discovered in 0.25 $\mu$m vias of a SiO$_2$ dual damascene electrical test lot from an unrelated experiment. Specifically, the voids were found while performing FIB/SEMs of via chain structures. Three classifications of vias were observed: Fully filled, partially filled, and completely discontinuous vias. Samples from each classification of vias were also evaluated by apparatus 1300 which successfully provided void measurements in via chains. Via void measurement is represented by symbolic drawings in FIGS. 18 and 20. Specifically, these symbolic drawings of via chains show copper segments M2 (signifying metal level 2) connected to an M1 (signifying metal level 1) copper segment by two vias in FIG. 18. M2 segments are separated by inter-metal dielectric (IMD) with segment M1 buried under the IMD.

Figure 18:
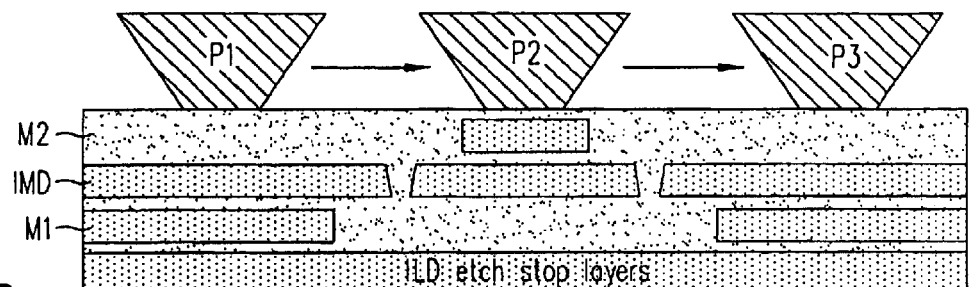
FIGS. 18 and 20 illustrate, in symbolic drawings, two structures evaluated using the method of FIG. 2.
Figure 19:
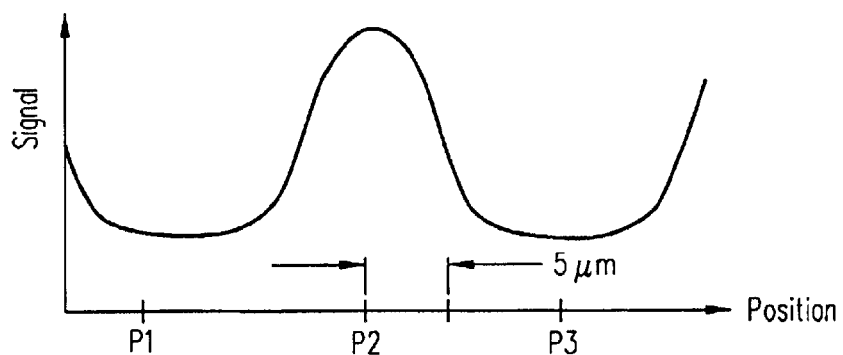
FIGS. 19 and 21 illustrate, in graphs, signals obtained by performance of the method of FIG. 2 on the corresponding structures illustrated in FIGS. 18 and 20.

A measurement of the type described above is made in a scan across an M2 copper segment (see position P1 in FIG. 18) then across a buried M1 copper segment (position P2), and finally across another M2 copper segment (position P3). The measurement signal is different for M2 segments as compared to M1 metal segments, as illustrated in FIG. 19. As noted above, the M1 reflectance signal (which is measured at position P2) is higher because the laser light is trapped when focused on the M1 layer between M2 segments, increasing the temperature more in the M1 metal as illustrated in FIG. 18. This characteristic higher reflectance can be seen at a regular frequency in the chart of FIG. 23 (see the structure with no voids illustrated in FIG. 22 that generated this measurement signal). Note that the baseline signal magnitude for the M2 metal in this via chain scan is around 15,000 $\mu$V/V. The signal is obtained as the lock-in amplifier 1325 output in $\mu$V divided by DC (direct current) voltage output of amplifier 1324 (the lock-in output normalized to the average reflectance of the sample; this normalization removes signal variation due to changes in reflectance caused by substrate or coating thickness variations).

Figure 20:
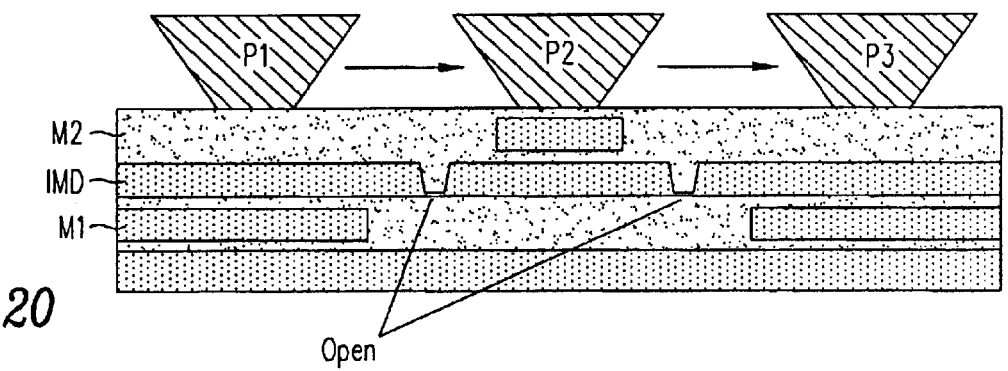

The symbolic drawings of FIG. 20 shows the response of a scan across a via chain when segment M2 is disconnected from segment M1 because of open vias. Thermal connectivity is disrupted resulting in localized heating in the vias and an increase in the measurement signal. Now, besides the local heating of segment M1, there is localized heating at regular intervals where the vias are located.

Figure 21:
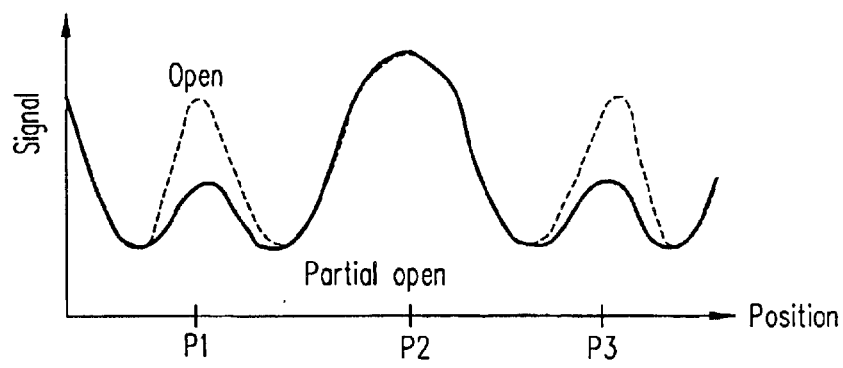

A linear scan across the via chain picks up the increase in frequency response due to localized heating. This increase in frequency is shown by the emergence of additional peaks at positions P1 and P3 in the chart of FIG. 21. When the voids are large enough, the magnitude of the new peaks approaches that of the original peak for open vias as illustrated by the dashed line in FIG. 21. Such strong new peaks are seen in FIG. 27, as compared to weaker new peaks for partial voids shown in FIG. 25.

Note the signal magnitude measured over traces in the M2 metal layer in this via chain scan increases with the degree of voiding, because less heat is conducted out and therefore the via chain becomes hotter. The baseline for a good via chain is about 15,000 $\mu$V/V (FIG. 23) as opposed to between 20,000 and 25,000 $\mu$V/V for via chains with voiding (see FIGS. 25 and 27). As used herein, the term "baseline" is used to indicate the lowest horizontal line in the graph (indicating a specific measured signal level) that is either crossed over or touched by at least a majority of the local minima in the measured signal (and in the example of FIG. 23 a line at 15,000 $\mu$V/V is touched or crossed by all of the local minima except for the local minima at the position 30 mm).

Figure 22:
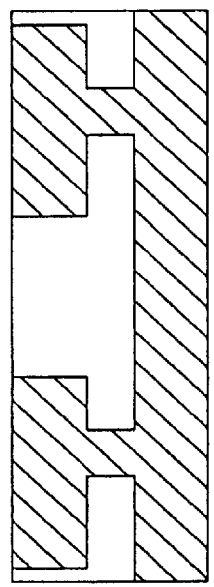
FIGS. 22, 24 and 26 illustrate, in symbolic drawings, additional structures evaluated using the method of FIG. 2.
Figure 23:
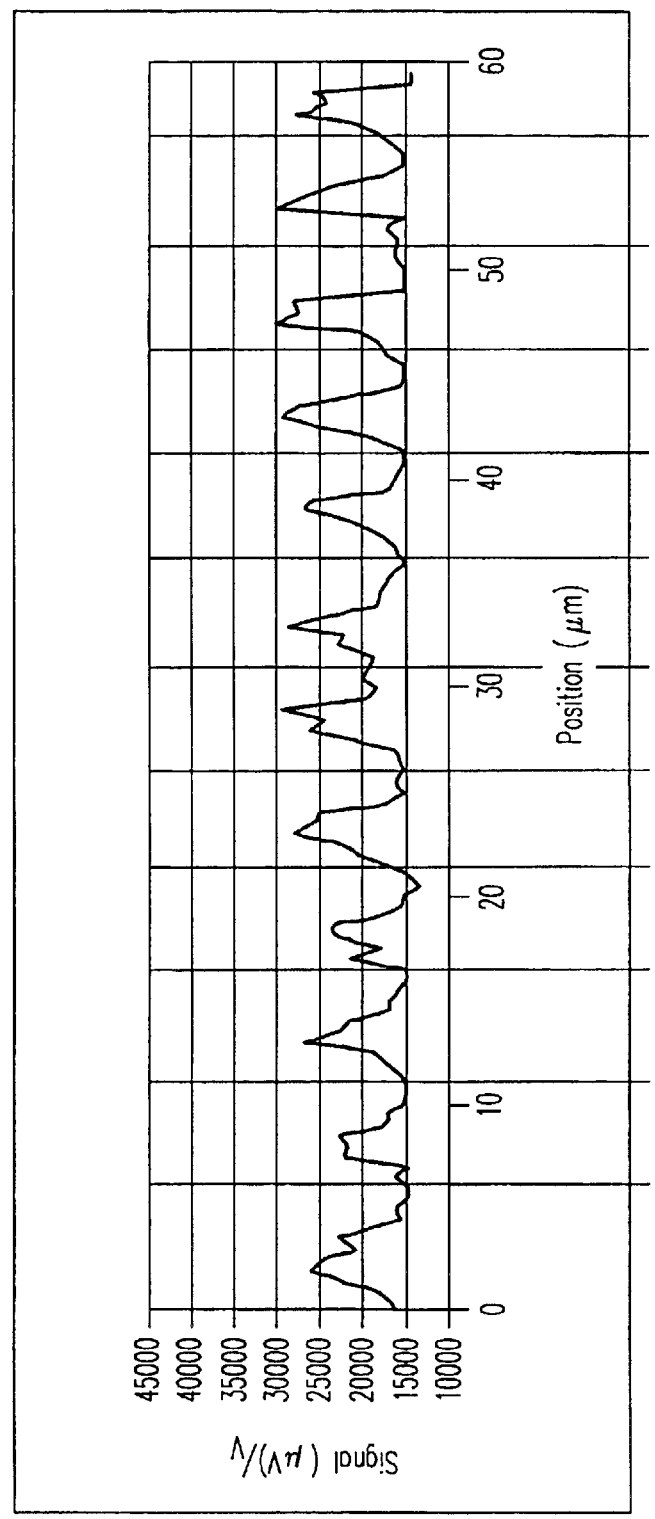
FIGS. 23, 25, and 27 illustrate, in graphs, signals obtained by performance of the method of FIG. 2 on the corresponding structures illustrated in FIGS. 22, 24 and 26 respectively.
Figure 24:
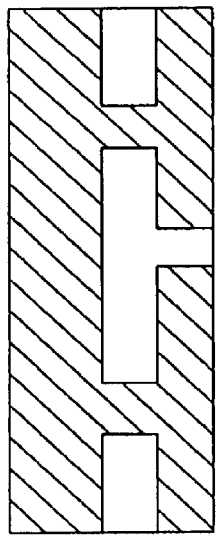
Figure 25:
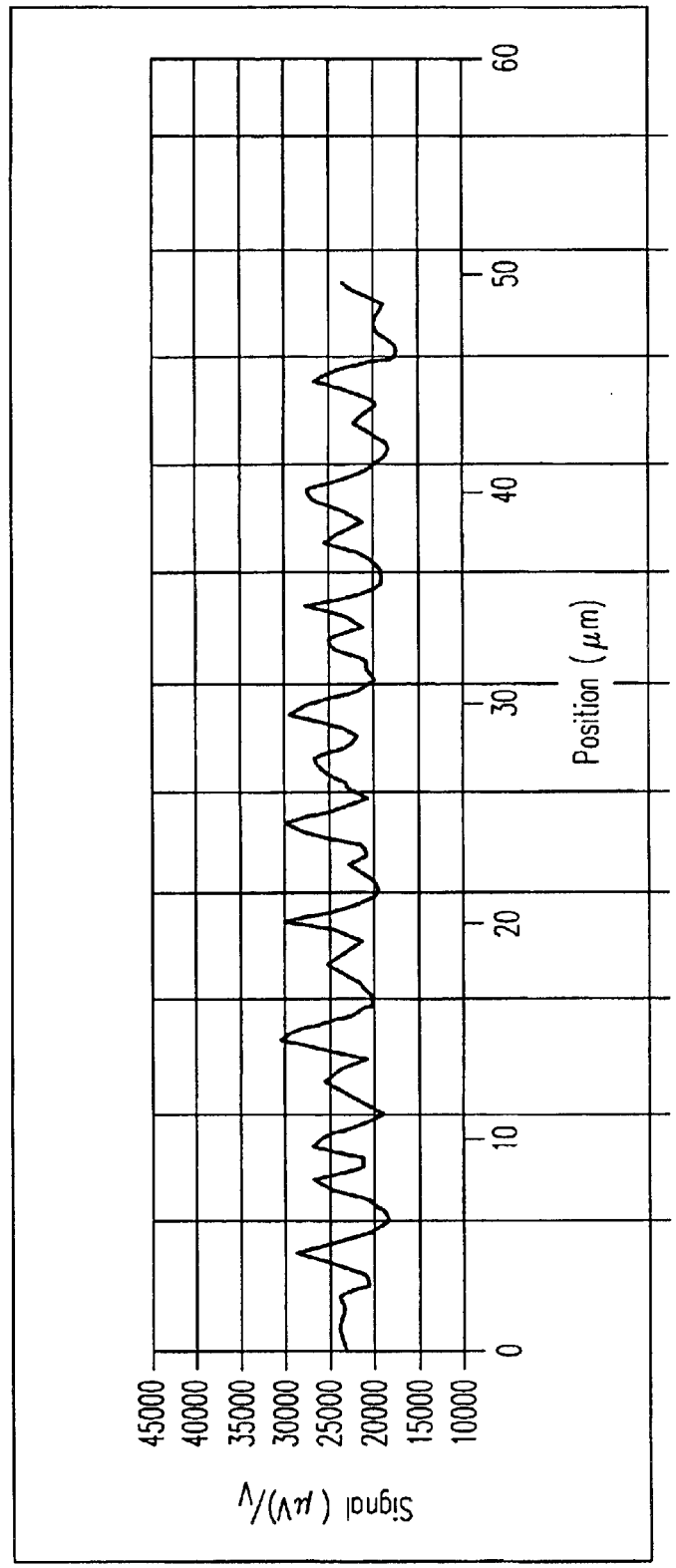
Figure 26:
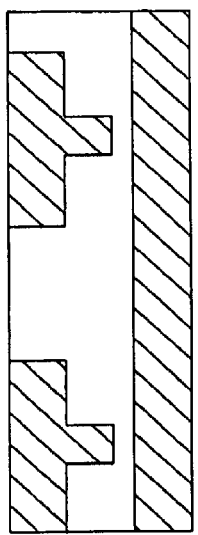
Figure 27:
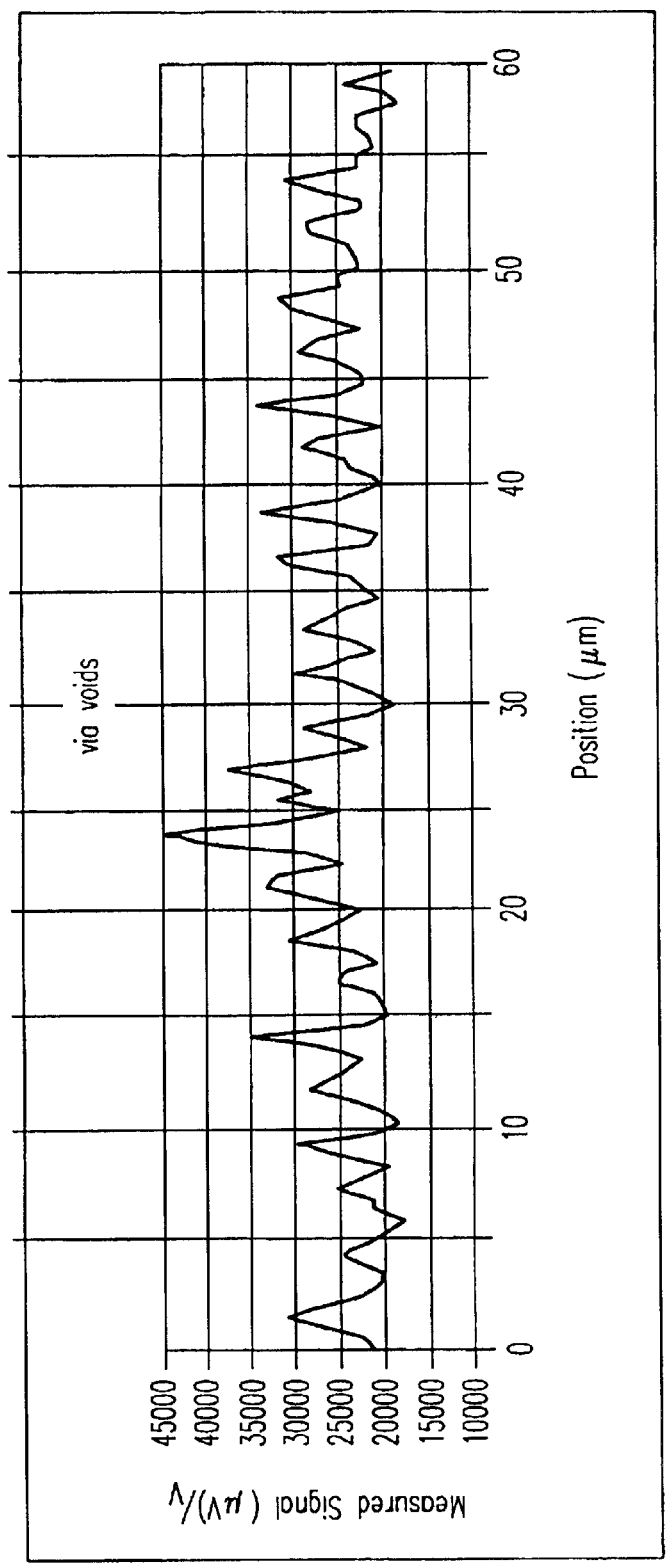

FIB-SEM cross section pictures in FIGS. 22, 24 and 26 confirm the corresponding indication by the measured signal for no void voids, partial voids, and fully open vias shown in the respective FIGS. 23, 25, and 27. The correspondence shows the ability of apparatus 1300 to differentiate between vias with no voids, and vias with some degree of voids.

The measurement signals obtained by apparatus 1300 for via chains on a dual damascene wafer with a porous ultra low-k IMD layer confirm the feasibility of evaluating the integrity (or defectiveness) of copper features on porous low-k films. In one example, voids were not intentionally fabricated in the copper. FIG. 28 shows the results of a 150 $\mu$m long via chain scan for a measurement of the type described herein. A characteristic single peak is observed for most of the scan. However, as shown on the middle-right section 2802 of the chart, double-peaked signals are detected (as compared to the single peaks in section 2801), indicating the likely discovery of via copper voids. Therefore, apparatus 1300 can be used with copper features on porous low-k inter-metal dielectric (IMD).

Work to date has been done on 0.25 $\mu$m vias. (See the vias in FIGS. 22, 24 and 26.) A set of wafers with very small vias (e.g. of diameter 0.15 $\mu$m) due to photo/etch problems was evaluated and the measurement was found to be sensitive to voids in such small features (the patterns appear similar to those described above).

Numerous modifications and adaptations of the embodiments described herein will be apparent to the skilled artisan in view of the disclosure. For example, in an apparatus of the type described herein, no laser beams may be used, for example if heat is applied by an electron beam and temperature is measured by a thermal imager.

Alternatively, heat may be applied by a probe that contacts the conductive structure being evaluated, and another probe that also contacts the structure may be used to measure the temperature, in an alternative embodiment.

In another embodiment, one laser is used for heating the conductive structure, and a thermal imager is used to measure the temperature profile. Furthermore, in yet another embodiment, electrical heating (using contact probes) is used to heat the conductive structure, and thermal imaging is used to evaluate the structure. Alternatively, heating could be applied using electrical contact probes, or by electron beam, and a laser may be used to measure the temperature change.

Furthermore, although in certain embodiments a via chain is evaluated by use of one or more methods of the type described herein, in other embodiments, other portions of a conductive structure that do not have any vias may be evaluated as described herein. Accordingly, numerous modifications, adaptations, and enhancements of the embodiments, implementations and examples described herein are encompassed by the attached claims.

Although in certain of the embodiments described above, beams 250 and 251 directly illuminate the conductive structure, in other embodiments the illumination can be indirect, e.g., through dielectric layer 2900 (FIG. 29). For example, beams 250 and 251 passed through dielectric layer 2900 to apply heat to and measure the temperature of trace 2901 in a manner similar to that described above. In the conductive structure illustrated in FIG. 29, traces 2901 and 2903 are oriented perpendicular to the plane of the paper, whereas traces 2905 and 2907 are oriented perpendicular to traces 2901 and 2903 (i.e. parallel to the plane of the paper, and running from left to right).

Therefore, direct contact of the type required in the prior art, for example by Smith, et al. in U.S. Pat. No. 5,228,776 is not required in certain embodiments. Elimination of direct contact by use of a method of the type described herein is advantageous because capping layers are often applied to protect the conductive structure (e.g. containing copper lines) from corrosion. Such capping layers prevent measurement with other methods, such as voltage contrast SEM. For example, the structures in FIGS. 22, 24 and 26 include a dielectric capping layer over the M2 copper lines. Also, as discussed earlier, voiding often results from thermal cycles associated with the formation of dielectric layers above the layer containing a via chain. A method of the type described herein is able to detect such voiding.

Furthermore, a method of the type described herein is insensitive to a bump or dimple on the surface of a trace when a number of traces are covered by a spot illuminated by beams 250 and 251, because the signal being measured is averaged over the traces covered by the spot. Therefore, in one embodiment of the type described herein the measured signal is less sensitive to bumps or dimples on the surface of a trace as compared to the method described by Smith et al. However, a bump or dimple would show up in a scan along a single line. This would be an isolated effect, and would not appear periodic in the scan.

Moreover, in addition to evaluating the integrity of via 2902 that is directly connected to trace 2901, as described above in certain embodiments, in other embodiments other vias such as via 2906 may also be evaluated in the manner described herein. Specifically, the temperature of trace 2901 is hotter if via 2906 is defective, as compared to similar measurement in reference wafer that has a well formed via 2906. Note, however, that dielectic layer 2900 must be at least partially transparent for such an embodiment. The degree of transparency should be sufficient to enable heating of traces, and measurement with the probe beam.

Furthermore, a signal measured on trace 2905 may be compared with a corresponding signal measured over trace 2907 to identify the integrity of the underlying vias 2906, 2908 and 2910. Also, beams 250 and 251 may be polarized along the direction of the length of traces 2901 and 2903, to ensure that trace 2905 is the trace to which heat is applied and of which the temperature is measured. For more information on use of polarized beams, see U.S. patent application Ser. No. 09/521,232 that has been incorporated by reference above.

Although a method has been described above in reference to a via chain including traces 2901 and 2903 (FIG. 29), any other conductive structure, such as the set of traces 14A–14L may also be evaluated in the same manner. The method is just as effective even though the width of a trace 14L is less than ½ of the width of a trace 2901. Also, such a method may be used to evaluate a conductive structure that is buried under a number of dielectric layers, such as structure 2920, as long as each of the dielectric layers is at least partially transparent sufficient for the passage of light therethrough.

Figure 31:
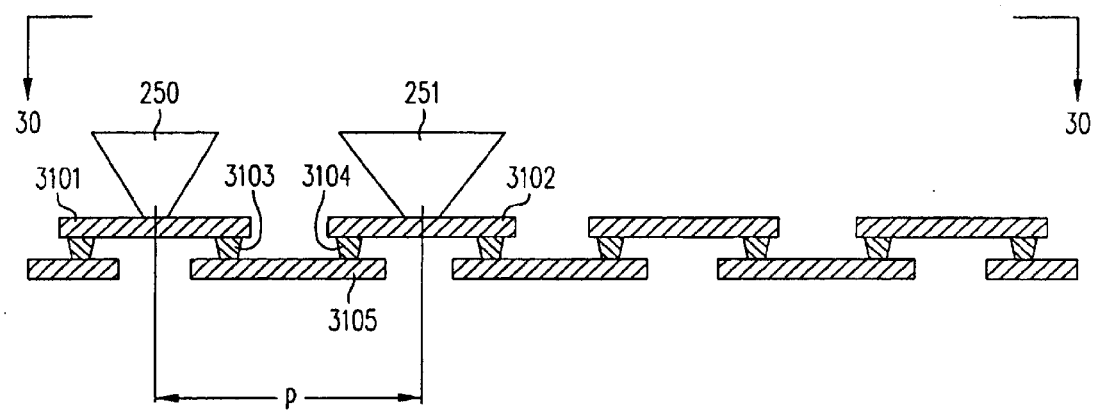
FIG. 31 illustrates, in a cross-sectional view along the direction 31—31 in FIG. 30, the via chain being evaluated by the separated laser beams.

Although in certain embodiments, beams 250 and 251 are coincident, in other embodiments beams 250 and 251 need not be coincident for example, as illustrated in FIGS. 30 and 31. Specifically, in FIGS. 30 and 31, beams 250 and 251 are scanned from left to right while separated from one another by a fixed distance p which is the pitch between two conductive traces 3101 and 3102 that are connected to one another by vias 3103 and 3104 and conductive trace 3105 (which is located in an underlying layer).

Note, however, that in an alternative embodiment, the distance between beams 250 and 251 may be half as much as in FIG. 31, e.g., half p. In this alternative embodiment, beams 250 and 251 respectively illuminate traces 3101 and 3105 that are respectively located in different metal layers of the conductive structure. This alternative embodiment distinguishes over the teachings of Smith et al. (described above) by scanning beams 250 and 251 in unison. Therefore, in this alternative embodiment, thermal waves may or may not be present depending on the implementation.

In yet another embodiment, the distance between beams 250 and 251 may be completely arbitrary, as long as the distance is kept fixed, e.g., during a scan, or when comparing a measurement from a production wafer with corresponding measurement in reference wafer. The distance between beams 250 and 251 may be selected so that only one via is evaluated during a single measurement, e.g., if the distance is 0.5 p, although in other embodiments a smaller distance may be used. In certain embodiments, the distance between beams 250 and 251 may be so small as to cause two spots that are formed on a wafer to contact one another, or the spots may even partially overlap.

Figure 32:
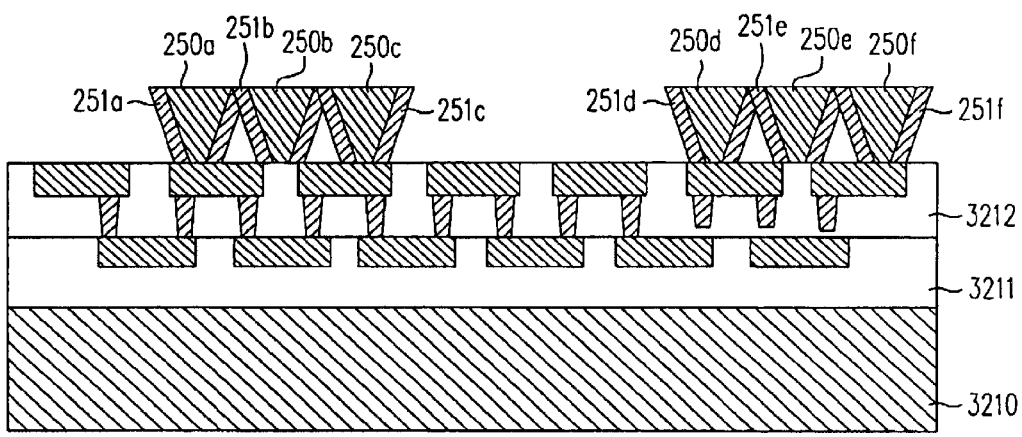
FIG. 32 illustrates, in a cross-sectional view, use of a number of laser beams to make simultaneous measurements of the type illustrated in FIG. 2.

Furthermore, in certain embodiments, a number of laser beams may be used simultaneously to perform a number of measurements at the same time, thereby to speed up the rate at which wafers are evaluated, so as to conform to the rate at which wafers are fabricated, as illustrated in FIG. 32.

Although in certain embodiments a signal measured by one of the above-described methods is analyzed, for example by performing Fourier transform and detecting the presence of a peak at twice the frequency required by the spatial pitch, in other embodiments other kind of analyses may be performed. For example, instead of performing a Fourier transform, any deviation of the measured signal from a periodic waveform may be deemed to indicate a defect, to be analyzed further. Such analysis can be, for example, of the above-described type, such as a Fourier transform that is analyzed for a maximum at twice the frequency, as would be apparent to a skilled engineer.

Depending on the structure being evaluated, the waveform may not be necessarily periodic, for example, see region 2801 (FIG. 28). In such structures, the signal obtained from measurement from such a structure may be compared with a signal obtained by performing the same measurement on a corresponding structure in a reference wafer, or alternatively the corresponding Fourier transforms may be compared (which may include multiple frequency components).

Figure 33:
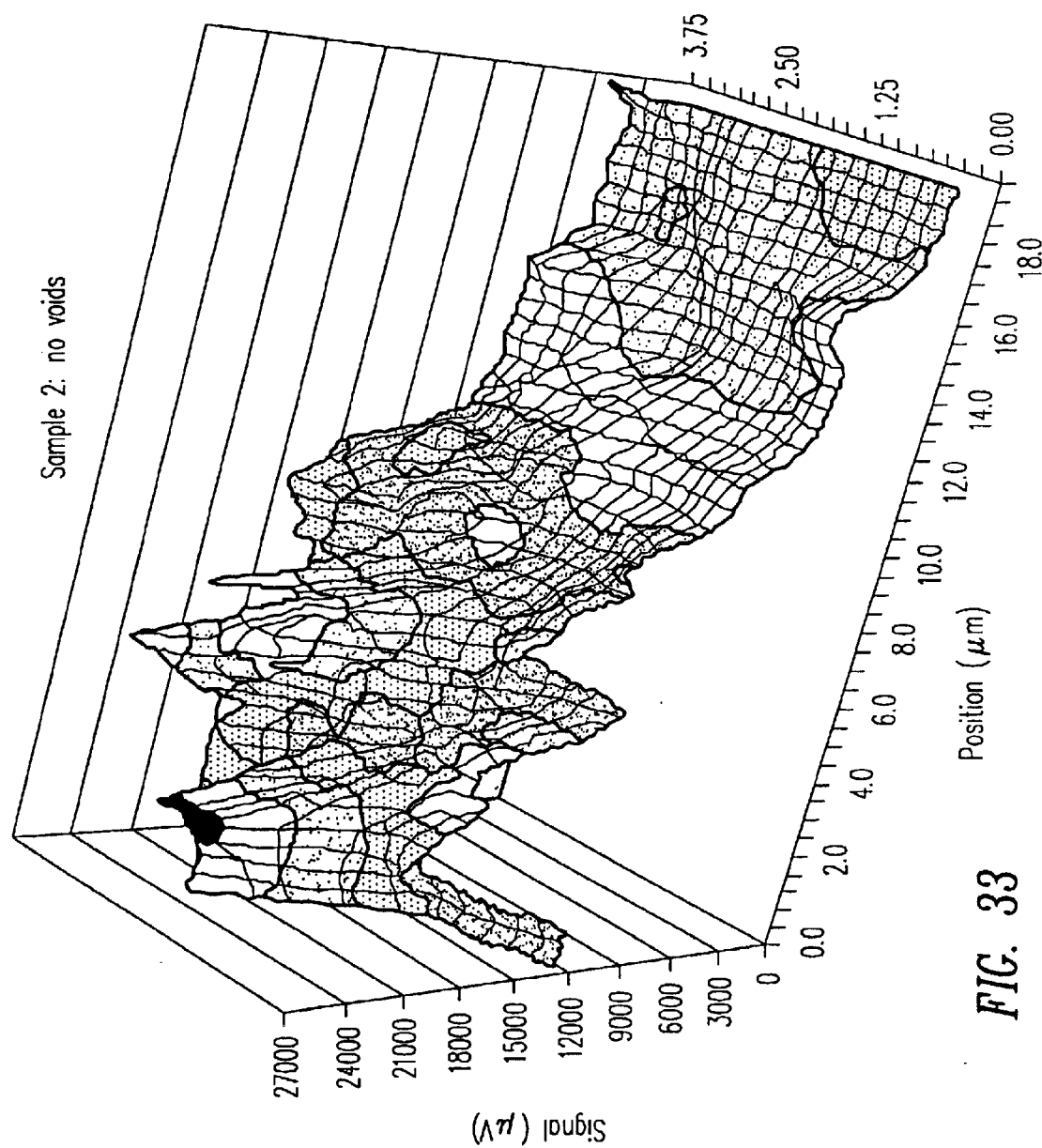
FIGS. 33 and 34 illustrate, in three dimensional graphs, area scans obtained by a method of the type described herein, from a structure having no voids and a structure having voids respectively.
Figure 34:
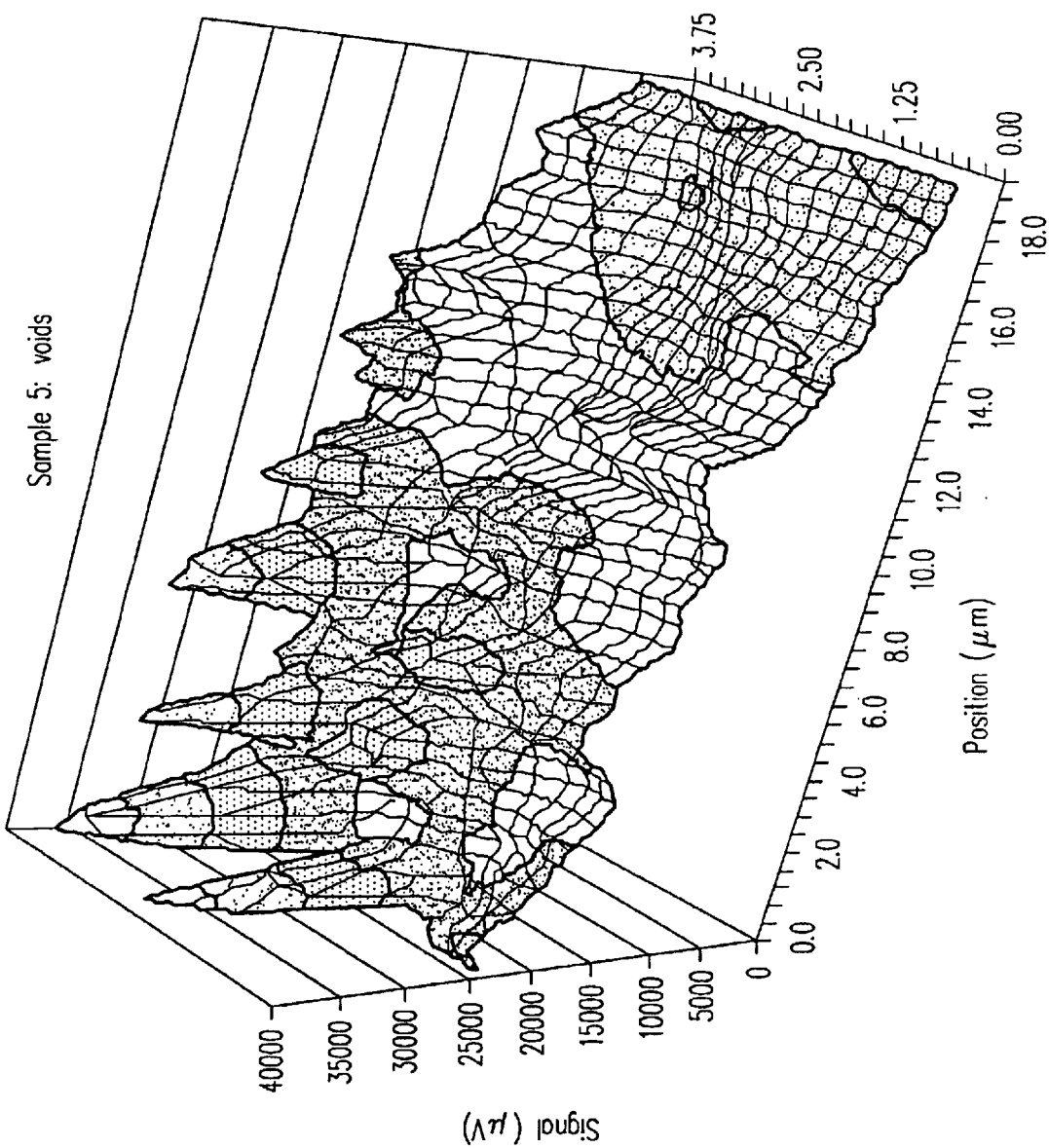

Moreover, a scanning measurement of the type described herein may be repeated multiple times along a number of parallel lines to obtain an area scan, thereby increasing the likelihood of finding a defect. For example, FIG. 33 illustrates an area scan from a good sample (corresponds to FIGS. 22 and 23) wherein a via chain is on the left. The lower region on the right of FIG. 33 is an area scan from a metal bus line connecting to the via chain. FIG. 34 illustrates a voided sample (corresponds to FIGS. 26 and 27). Note that in FIG. 34 there are double the number of peaks from the above example in FIG. 33. Such non-destructive testing along multiple lines is not available in several of the prior art methods, such as the method described by Smith et al. (described above).

Furthermore, instead of analysis by a computer, a plot of the measured signal as a function of position can be inspected manually, by an operator who may visually detect a change in the signal, thereby to identify the location of a defect.

Note that a method of identifying a defect as described herein, although used with via chains in one embodiment, in other embodiments, any structure that shunts heat flow can be evaluated, and a via chain is just one example of such a structure.

Also, although in certain embodiments, a scan is made along a straight line, scans of the type described herein can be made along any contour (such as a circle), depending on the structure of the wafer under evaluation.

Moreover, comparison of measurements need not be with a reference wafer and instead can be with a test structure formed on the production wafer adjacent to the conductive structure under evaluation (e.g. in the same die or outside the die). Furthermore, baseline comparison may also be performed to evaluate a conductive structure. As noted earlier, the baseline in FIG. 23 is 15,000 $\mu$V/V and rises in FIGS. 25 and 27 with voiding. Also note an irregular baseline in the case of worst voiding illustrated in FIG. 27.

Furthermore, methods of the type described herein are used in other embodiments in scanning periodic structures. Also, some embodiments evaluate a structure with periodicity and vias, but that structure is not a via chain, e.g. two continuous metal lines with evenly spaced connections, or with connections that are not evenly spaced. Also, an irregularity can be determined by direct comparison with a known good scan regardless of spacing of the structure. Numerous such modifications and adaptations of the embodiments, examples and implementations described herein are encompassed by the attached claims.

What is claimed is:

1. A method of identifying presence or absence of a defect in a semiconductor wafer, the method comprising:

applying heat to a conductive structure formed on said semiconductor wafer, said conductive structure being periodic in space along a direction;

measuring a signal indicative of temperature of a portion of the conductive structure heated by conduction of the applied heat therethrough, thereby to obtain a measurement;

repeating the act of measuring at each of a number of different locations on the conductive structure, thereby to obtain a plurality of measurements, wherein said locations are along said direction; and determining absence of the defect in the conductive structure, on finding periodicity in the plurality of measurements, wherein said periodicity is related to periodicity of the conductive structure.

2. The method of claim 1, wherein:

a laser beam is used during said applying of heat;

reflection of another laser beam is measured during said measuring; and the laser beams are scanned together during said measuring.

3. The method of claim 2, wherein:

the laser beams are coincident, thereby to form a single spot on the conductive structure.

4. The method of claim 1, wherein:

the conductive structure has at least one dimension less than 1 $\mu$m.

5. The method of claim 1, wherein:

an electron beam is used during said applying of heat.

6. The method of claim 1, wherein:

a thermal imager is used during said measuring.

7. The method of claim 1, wherein:

said determining includes using a transform of said plurality of measurements, said transform converting said plurality of measurements from a spatial domain into a frequency domain.

8. The method of claim 1, wherein:

said determining includes identifying a frequency component not found in a corresponding plurality of measurements from a reference wafer.

9. The method of claim 1, wherein:

said determining includes comparing a curve defined by said plurality of measurements to a reference curve defined by a corresponding plurality of measurements from a reference wafer.

10. The method of claim 1, wherein:

said determining includes comparing a curve defined by said plurality of measurements to a baseline.

11. The method of claim 1, wherein:

a measurement is performed at least at a plurality of vias located sequentially one after another in said direction.

12. The method of claim 1, wherein:

a pump beam is incident on a first trace in the conductive structure during said applying; and a probe beam is incident on a second trace in said conductive structure during said measuring; and wherein said first trace is coupled to said second trace through at least one via.

13. The method of claim 12, wherein:

each of said first trace and said second trace are in a single metal layer.

14. The method of claim 12, wherein:

each of said first trace and said second trace are in different metal layers.

15. The method of claim 1, wherein:

said determining includes comparing the plurality of measurements to a corresponding plurality of measurements obtained from a reference wafer.

16. The method of claim 1, wherein:

said repeated acts of measuring are performed while moving a stage carrying the semiconductor wafer containing the conductive structure; and performing said measuring continuously, thereby to obtain an analog signal; and using said analog signal during said determining.

17. A method for determining the quality of a first conductive structure, the method comprising:

applying heat to the first conductive structure using a modulated heat source, said first conductive structure being periodic in space along a direction;

measuring a first phase difference between temperature change of said first conductive structure and modulation of said heat source; and analyzing whether said phase difference is larger than a second phase difference, said second phase difference being detected with a second conductive structure that is non-defective, to determine quality of said first conductive structure.

18. The method of claim 17 wherein reflection of a laser beam is used to measure the phase difference.

19. The method of claim 17 wherein said quality is related to a defect in said first conductive structure.

20. The method of claim 19 wherein said defect is any defect in a group consisting of voiding, narrow trace, and misalignment of a via to a trace.

21. The method of claim 17 wherein a pump beam is used in said applying, and a probe beam is used in said measuring, and wherein:

the pump beam and the probe beam form spots on said first conductive structure that at least partially overlap each other.

22. The method of claim 17 wherein a pump beam is used in said applying, and a probe beam is used in said measuring, the method further comprising:

scanning the pump beam in unison with the probe beam.

23. The method of claim 22 wherein:

the pump beam illuminates a first trace in a first metal layer of the first conductive structure; and the probe beam illuminates a second trace in a second metal layer of the first conductive structure.

24. The method of claim 22 wherein:

the pump beam illuminates a first trace in a first metal layer of the first conductive structure; and the probe beam illuminates said first trace in said first metal layer of the first conductive structure.

25. The method of claim 22 wherein:

the pump beam illuminates a first trace in a first metal layer of the first conductive structure; and the probe beam illuminates a second trace in said first metal layer of the first conductive structure.

26. A method for determining the quality of a conductive structure, the method comprising:

applying heat to the conductive structure using a modulated heat source, wherein said conductive structure comprises a plurality of via chains, and the heat is applied simultaneously to more than one via chain;

varying the frequency of modulation of said heat source;

measuring a change in temperature of said conductive structure, as a function of the frequency of modulation; and analyzing said function to determine the quality of said conductive structure.

27. The method of claim 26, wherein reflection of a laser beam is used to measure the temperature change.

28. The method of claim 26, wherein heat is applied to said conductive structure using a laser beam.

29. The method of claim 26, further comprising:

repeating the act of measuring at each of a number of different locations on the conductive structure, thereby to obtain a plurality of measurements; and using said plurality of measurements during said analyzing.

30. The method of claim 26 further comprising:

moving a stage carrying a semiconductor wafer containing the conductive structure at a fixed speed; and performing said act of measuring continuously, thereby to obtain an analog signal; and using said analog signal during said analyzing.

31. The method of claim 26 wherein said analyzing comprises:

identifying irregular features in the conductive structure.

32. An apparatus for identifying a defect in a conductive structure, the apparatus comprising:

a laser for applying heat to the conductive structure, the conductive structure being periodic in space along a direction;

a sensor for measuring a signal indicative of temperature of a portion of the conductive structure heated by conduction of the applied heat therethrough, at a number of different locations on the conductive structure, thereby to obtain a plurality of measurements, wherein said locations are along said direction; and means for determining presence of the defect in the conductive structure, based on finding aperiodicity in the plurality of measurements.

33. The apparatus of claim 32, wherein said sensor for measuring comprises a thermal imager.

34. The apparatus of claim 32 wherein said means for determining comprises a personal computer.

35. The method of claim 1 wherein:
a spatial frequency of the plurality of measurements is equal to inverse of the periodicity of the conductive structure.

36. A method of identifying a defect in a semiconductor wafer, the method comprising:
using a first beam to apply heat to a conductive structure formed on said semiconductor wafer, the conductive structure being periodic in space;
using a second beam to measure a signal indicative of temperature of a portion of the conductive structure heated by conduction of the applied heat therethrough, thereby to obtain a measurement;
repeating the act of measuring at each of a number of different locations on the conductive structure, thereby to obtain a plurality of measurements; and
determining presence of the defect in the conductive structure, depending on spatial periodicity of the plurality of measurements;
wherein the first beam and the second beam are at least partially coincident.

37. The method of claim 36 wherein:
the first beam and the second beam are perfectly coincident, thereby to form a single spot on the conductive structure.

38. A method for determining the quality of a first conductive structure, the method comprising:
applying heat to the first conductive structure using a modulated heat source, said first conductive structure being periodic in space along a direction;
measuring a first chase difference between temperature change of said first conductive structure and modulation of said heat source; and
analyzing whether said phase difference is larger than a second phase difference, said second chase difference being detected with a second conductive structure that is non-defective, to determine quality of said first conductive structure;
wherein;
the heat source is modulated at a frequency selected to be sufficiently low to prevent generation of a thermal wave.

* * * * *